US012767696B2

(12) United States Patent
Jeong et al.

(10) Patent No.: US 12,767,696 B2
(45) Date of Patent: Oct. 20, 2026

(54) RECOMBINANT PROTEIN HAVING FUSED INTERFERON-BETA MUTEIN AND ANTIBODY, AND PHARMACEUTICAL COMPOSITION COMPRISING SAME

(71) Applicant: ABION INC., Seoul (KR)

(72) Inventors: Hae Min Jeong, Seoul (KR); Chan Gyu Lee, Seoul (KR); Ji Sun Lee, Seoul (KR); Jun Young Choi, Seoul (KR); Na Young Kim, Seoul (KR); Yong Jin Lee, Seoul (KR)

(73) Assignee: ABION INC., Seoul (KR)

(*) Notice: Subject to any disclaimer, the term of this patent is extended or adjusted under 35 U.S.C. 154(b) by 802 days.

(21) Appl. No.: 17/922,179

(22) PCT Filed: Apr. 28, 2021

(86) PCT No.: PCT/KR2021/005407

§ 371 (c)(1),
(2) Date: Oct. 28, 2022

(87) PCT Pub. No.: WO2021/221470

PCT Pub. Date: Nov. 4, 2021

(65) Prior Publication Data

US 2024/0270807 A1 Aug. 15, 2024

(30) Foreign Application Priority Data

Apr. 29, 2020 (KR) ........................ 10-2020-0052911

(51) Int. Cl.

| | |
|---|---|
| ***C07K 14/565*** | (2006.01) |
| ***A61K 38/00*** | (2006.01) |
| ***A61K 39/00*** | (2006.01) |
| ***A61P 35/00*** | (2006.01) |
| ***C07K 16/32*** | (2006.01) |
| ***C12N 15/85*** | (2006.01) |

(52) U.S. Cl.

CPC ............ *C07K 14/565* (2013.01); *A61K 39/00* (2013.01); *A61P 35/00* (2018.01); *C07K 16/32* (2013.01); *C12N 15/85* (2013.01); *A61K 38/00* (2013.01); *A61K 2039/505* (2013.01); *C07K 2317/24* (2013.01); *C07K 2317/732* (2013.01); *C07K 2319/33* (2013.01); *C07K 2319/35* (2013.01)

(58) Field of Classification Search

CPC .. C07K 14/565; C07K 16/32; C07K 2317/24; C07K 2317/732; C07K 2319/33; C07K 2319/35; C07K 2317/73; C07K 2319/00; C07K 14/52; A61K 39/00; A61K 38/00; A61K 2039/505; A61K 39/39; A61P 35/00; A61P 31/12; C12N 15/85; C12N 15/62

See application file for complete search history.

(56) References Cited

U.S. PATENT DOCUMENTS

| | | | | |
|---|---|---|---|---|
| 4,588,585 A * | 5/1986 | Mark | ...................... | C07K 14/55 435/69.51 |
| 7,670,595 B2 * | 3/2010 | Gillies | .................... | A61P 37/02 536/23.4 |
| 2006/0228332 A1 | 10/2006 | Gillies et al. | | |
| 2019/0194284 A1 | 6/2019 | Kley et al. | | |

FOREIGN PATENT DOCUMENTS

| | | | | |
|---|---|---|---|---|
| EP | 0218825 A1 | 4/1987 | | |
| EP | 3266801 A1 | 1/2018 | | |
| JP | 2008-508862 A | 3/2008 | | |
| KR | 10-0781666 B1 | 12/2007 | | |
| KR | 10-2016-0107070 A | 9/2016 | | |
| KR | 10-2018-0025743 A | 3/2018 | | |
| WO | 2004020468 A2 | 3/2004 | | |
| WO | WO-2007110231 A2 * | 10/2007 | .............. | A61P 31/12 |
| WO | WO-2016140528 A1 * | 9/2016 | ............. | C07K 19/00 |
| WO | WO-2016163764 A2 * | 10/2016 | ............. | A61K 47/16 |

OTHER PUBLICATIONS

Uniprot P01577 IFNB3_BOVIN, bovine interferon beta, accessed Sep. 22, 2025 (Year: 2025).*
Uniprot P01574 IFNB_Human, human interferon beta, accessed Sep. 22, 2025 (Year: 2025).*
Fridman, W.H., 1991. Fc receptors and immunoglobulin binding factors 1. The FASEB journal, 5(12), pp. 2684-2690 (Year: 1991).*
Chiu et al. Antibodies 2019 8, 55, 1-80 (Year: 2019).*
Borden EC. Interferons α and β in cancer: therapeutic opportunities from new insights. Nat Rev Drug Discov. Mar. 2019; 18(3):219-234. doi: 10.1038/s41573-018-0011-2. PMID: 3067980 (Year: 2019).*
Lee JI, Eisenberg SP, Rosendahl MS, Chlipala EA, Brown JD, Doherty DH, Cox GN. Site-specific PEGylation enhances the pharmacokinetic properties and antitumor activity of interferon beta-1b. J Interferon Cytokine Res. Dec. 2013;33(12):769-77. doi: 10.1089/jir.2012.0148. Epub Aug. 20, 2013. (Year: 2013).*
Kay M, Hasan-Abad AM, Hojati Z, Korbekandi H. Targeted mutations in Val101 and Arg27 interferon beta protein increase its transcriptional and translational activities. Cytokine. Feb. 2016;78:1-6. doi: 10.1016/j.cyto.2015.11.019. Epub Nov. 23, 2015. PMID: 26615566 (Year: 2015).*

(Continued)

*Primary Examiner* — Gregory S Emch
*Assistant Examiner* — Kathleen Cunningchen
(74) *Attorney, Agent, or Firm* — Meunier Carlin & Curfman LLC

(57) ABSTRACT

The present invention relates to: a recombinant protein in which an interferon-beta mutein, in which an amino acid residue is substituted, and an antibody binding to a specific antigen are fused together; and a pharmaceutical composition for treating cancer, the composition comprising, as active ingredients, a polynucleotide, an expression vector and a recombinant microorganism, and the recombinant protein. In the recombinant protein, the physical properties of interferon-beta are improved through site-specific mutation, and thus the recombinant protein may have improved biological activity and purification efficiency, and the productivity thereof can be increased.

12 Claims, 14 Drawing Sheets

Specification includes a Sequence Listing.

(56) References Cited

OTHER PUBLICATIONS

Bioinformatics.org "Sequence Manipulation Suite: Reverse Translate", reverse translation of SEQ ID No. 1, available at www.bioinformatics.org/sms2/rev_trans.html, published 2004, tool used Sep. 22, 2025 (Year: 2004).*
Yang X, et. al. Targeting the tumor microenvironment with interferon-β bridges innate and adaptive immune responses. Cancer Cell. Jan. 13, 2014;25(1):37-48. doi: 10.1016/j.ccr.2013.12.004. PMID: 24434209; PMCID: PMC3927846 (Year: 2014).*
Janeway, Immunobiology The Immune System in Health and Disease, 5th edition, 2001, Chapter 3 (Year: 2001).*
Runkel, et al. Structural and functional differences between glycosylated forms of human interferon-β (IFN-B). Pharmaceutical Research (1998), 15:4, p. 641-649 (Year: 1998).*
WO2016140528 Patentscope Machine Translation (Year: 2016).*
WO2016163764 Google machine translation (Year: 2016).*
Chu, "Improvement of Purification efficiency by site-directed mutagenesis in interferon beta mutein fusion antibody", Department of Molecular Medicine and Biopharmaceutical Sciences, Graduate School of Convergence Science and Technology, and College of Pharmacy, Seoul National University (2019).
International Search Report and Written Opinion received in PCT/KR2021/005407 dated Aug. 9, 2021, 20 pages.
Kim, Tae-Eun "The study for interferon beta-1a-based anti-cancer therapeutics," pp. 1-129.
Lee et al. "Antibody-based targeting of interferon-beta-1a mutein in HER2-positive cancer enhances antitumor effects through immune responses and direct cell killing", Frontier in Pharmacology, Jan. 8, 2021, vol. 11, Article 608774, pp. 1-16.
Song et al., Glycoengineering of Interferon-β 1a Improves Its Biophysical and Pharmacokinetic Properties, Plos One, May 23, 2014, 11 pages.
Extended European Search Report for European Application No. 21797179.5, dated Apr. 26, 2024, 16 Pages.
Lin, B., et al., Acidic pH and High-H2O2 Dual Tumor Microenvironment-Responsive Nanocatalytic Graphene Oxide for Cancer Selective Therapy and Recognition, ACS Appl. Mater. Interfaces, 2019, 10 pages.

* cited by examiner

| | Trastuzumab-IFNβ | Trastuzumab-IFNβ-R27T |
|---|---|---|
| Peak 1 (Aggregation) | 85% | 40% |
| Peak 2 (Target protein) | 15% | 60% |

| | Trastuzumab-IFNβ-R27T | Trastuzumab-IFNβ-C17S-R27T |
|---|---|---|
| Peak 1 (Aggregation) | 40% | 8% |
| Peak 2 (Target protein) | 60% | 92% |

| | Cetuximab-IFNβ-R27T | Cetuximab-IFNβ-C17S-R27T |
|---|---|---|
| Peak 1 (Aggregation) | 83% | 26.5% |
| Peak 2 (Target protein) | 17% | 73.5% |

| | Atezolizumab-IFNβ-R27T | Atezolizumab-IFNβ-C17S-R27T |
|---|---|---|
| Peak 1 (Aggregation) | 49% | 12.5% |
| Peak 2 (Target protein) | 51% | 87.5% |

| Subtype | Cell line | Trastuzumab | | Kadcyla (T-DM1) | | Trastuzumab-IFNβ-C17S-R27T | |
|---|---|---|---|---|---|---|---|
| | | IC50 (pM) | Max Inhibition (%) | IC50 (pM) | Max Inhibition (%) | IC50 (pM) | Max Inhibition (%) |
| HER2 high | NCI-N87 | 176 | 51.2 | 320 | > 100 | 46 | 96.2 |
| HER2 medium | SNU1 | - | - | > $10^5$ | 68.3 | 1.8 | 45.5 |
| | SNU620 | - | - | > $10^5$ | 53.9 | 0.4 | 88.3 |
| HER2 low | HS746T | - | - | > $10^5$ | 59.8 | 1.6 | 34.4 |
| | MKN45 | - | - | > $10^5$ | 38.9 | 2.1 | 50.3 |

| Experiments | STD | Trastuzumab-IFNβ | Trastuzumab-IFNβ-R27T | Trastuzumab-IFNβ-C17S-R27T |
|---|---|---|---|---|
| 1 | 6.39 | > 100 | 28.47 | 10.15 |
| 2 | 6.06 | > 100 | 20.67 | 6.98 |
| 3 | 6.58 | > 100 | 20.59 | 7.49 |
| 4 | 6.78 | > 100 | 25.75 | 8.55 |
| 5 | 5.86 | > 100 | 21.31 | 8.65 |
| **AVG** | **6.33** | **> 100** | **23.36** | **8.36** |
| CV | 5.9% | - | 15.3% | 14.6% |

| Group | Average tumor volume (31 day) |
|---|---|
| Control IgG (10 mg/kg) | 936.4 $mm^3$ |
| Trastuzumab-IFNβ-R27T (10 mg/kg) | 388.8 $mm^3$ |
| Trastuzumab-IFNβ-C17S-R27T (1 mg/kg) | 412.6 $mm^3$ |
| Trastuzumab-IFNβ-C17S-R27T (3 mg/kg) | 164.3 $mm^3$ |
| Trastuzumab-IFNβ-C17S-R27T (10 mg/kg) | 39.5 $mm^3$ |

RECOMBINANT PROTEIN HAVING FUSED INTERFERON-BETA MUTEIN AND ANTIBODY, AND PHARMACEUTICAL COMPOSITION COMPRISING SAME

SEQUENCE LISTING

A Sequence Listing conforming to the rules of WIPO Standard ST.25 is hereby incorporated by reference. Said Sequence Listing has been filed as an electronic document via EFS-Web in ASCII formatted text. The electronic document, created on Apr. 23, 2023, is entitled "11239-014US1_ST25", and is 27,017 bytes in size.

TECHNICAL FIELD

This application is a national stage application filed under 35 U.S.C. § 371 of PCT/KR2021/005407 filed Apr. 28, 2021, which claims the priority of Korean Patent Application No. 10-2020-0052911, filed on Apr. 29, 2020, the entirety of which are a reference of the present application.

The present invention relates to a recombinant protein in which an interferon-beta mutein, in which an amino acid residue is substituted, and an antibody binding to a specific antigen are fused together, a polynucleotide thereof, an expression vector and a host cell thereof, and a pharmaceutical composition for treating cancer comprising the recombinant protein as an active ingredient.

BACKGROUND ART

Interferon (IFN) is one of main cytokines that play an important role in immunity, and is known to have a strong anticancer effect. Such interferon is classified into Type I (IFN-α and IFN-β), Type II (IFN-γ), and Type III (IFN-λ).

Type I interferon exhibits antiviral and antiproliferative effects, and also plays an essential role even in cancer immunosurveillance as a function of recognizing a tumor-specific antigen to remove tumor cells.

Signaling of Type I interferon is a stepwise activation of a plurality of enzymes by the activity of interferon receptors, and at this time, transcription factors such as STAT1 and STAT2 also act. This signaling operates an immune system, and is required even to exhibit anticancer effects on various anticancer agents, such as chemotherapeutics such as anthracycline, antibodies targeting growth factor receptors such as human epidermal growth factor receptor 2 (HER2) and epidermal growth factor receptor (EGFR), administration of adjuvants, oncolytic virotherapy, and the like. In particular, Trastuzumab is an antibody cancer therapeutic agent that targets HER2, and is resistant to treatment due to overexpression of MUC4. One of signaling materials involved in such a resistance mechanism, pSTAT3, has a form (pSTAT3 homodimer) polymerized with two identical materials, and is known to be inhibited by pSTAT1. Accordingly, when Type I interferon that activates pSTAT1 is bound to Trastuzumab, increased anticancer efficacy may be expected.

Interferon-beta (IFN-β) has a stronger cell growth inhibitory effect than interferon-alpha (IFN-α). In particular, when used together with an anticancer agent, an antiproliferative activity range and a synergistic effect of interferon-beta are very excellent. However, it is known that the therapeutic agent using interferon has high cytotoxicity to exhibit symptoms such as fever (80%), myalgia (73%), headache (50%), fatigue (50%), malaise (50%), etc. from a subject to be treated. In addition, interferon-beta is a protein with strong hydrophobicity, and tends to be aggregated well to lower the biological activity and productivity. In addition, the interferon-beta has a short half-life, so that there is a disadvantage of being administered frequently. Therefore, in order to develop a therapeutic agent using interferon, it is necessary to minimize a limitation caused by interferon.

Accordingly, the present inventors have developed mutant interferon-beta with improved productivity and reduced aggregation by changing the physical properties of interferon through a site-specific mutation. Such an interferon-beta mutein may be fused with an antibody cancer therapeutic agent to be used as a new anticancer therapeutic agent that exhibits an excellent anticancer effect.

DISCLOSURE

Technical Problem

An aspect of the present invention is to provide a recombinant protein comprising an interferon-beta (IFN-β) mutein in which an amino acid residue at position 17 is substituted with serine and an amino acid residue at position 27 is substituted with threonine; and an antibody or a fragment thereof directly or indirectly covalently bound to the interferon-beta mutein.

Another aspect of the present invention is to provide a polynucleotide encoding the recombinant protein.

Another aspect of the present invention is to provide an expression vector comprising the polynucleotide.

Another aspect of the present invention is to provide a host cell transformed with the expression vector.

Another aspect of the present invention is to provide a pharmaceutical composition for treating cancer comprising the recombinant protein as an active ingredient.

Another aspect of the present invention is to provide a pharmaceutical composition for treating cancer consisting of the recombinant protein.

Another aspect of the present invention is to provide a pharmaceutical composition for treating cancer essentially consisting of the recombinant protein.

Yet another aspect of the present invention is to provide a method for increasing protein stability during production or isolation and purification of the recombinant protein, the method comprising:

(a) culturing a host cell transformed to express a recombinant protein comprising an antibody or a fragment thereof directly or indirectly covalently bound to an interferon-beta mutein; and (b) isolating and purifying the recombinant protein comprising the antibody or the fragment thereof directly or indirectly covalently bound to the interferon-beta mutein from the cultured host cell or a culture product thereof, wherein in the preparing of the recombinant protein comprising the antibody or the fragment thereof directly or indirectly covalently bound to the interferon-beta mutein, the host cell is transformed to express the recombinant protein in which amino acid 17, cysteine of the interferon-beta mutein is modified to another amino acid.

Still another aspect of the present invention is to provide the use of the recombinant protein for preparing an anticancer agent.

Still yet another aspect of the present invention is to provide a method for treating cancer comprising administering an effective amount of the composition comprising the recombinant protein to a subject in need thereof.

Technical Solution

According to an exemplary embodiment of the present invention, there is provided a recombinant protein comprising an interferon-beta (IFN-β) mutein in which an amino acid residue at position 17 is substituted with serine and an amino acid residue at position 27 is substituted with threonine; and an antibody or a fragment thereof directly or indirectly covalently bound to the interferon-beta mutein.

Interferon-beta is a globular protein with 5 alpha helices and is 22 kDa in size. In addition, the interferon-beta has various immunological activities, such as antiviral activity, cell growth inhibition or antiproliferative activity, lymphocyte cytotoxicity enhancing activity, immunomodulatory activity, target cell differentiation induction or inhibitory activity, macrophage activation activity, increased activity of cytokine production, increased activity of cytotoxic T cell effect, increased activity of natural killing cells, etc. Accordingly, it is reported that the interferon-beta is effective in treating cancer, autoimmune disorders, viral infections, diseases related to HIV, hepatitis C, rheumatoid arthritis, and the like. However, the interferon-beta is a strong hydrophobic protein, and exhibits an aggregation phenomenon, has low biological activity and productivity, and has a short half-life, so that there is a limitation in application of interferon-beta. Accordingly, in the present invention, by inducing site-directed mutagenesis with respect to a gene of interferon-beta, as compared with wild-type interferon-beta in which mutation does not occur, an interferon-beta mutein with improved physical properties was developed.

In the interferon-beta mutein, Cysteine (C) at position 17 is substituted with serine (S), and Aarginine (R) at position 27 is substituted with threonine (T) to include glycosyl groups in amino acid residues at positions 80 and 25. In this case, the interferon-beta mutein may be defined by an amino acid sequence of SEQ ID NO: 1 or a nucleotide sequence of SEQ ID NO: 2 encoding the same. Such an interferon-beta mutein includes all or part of an amino acid sequence of wild-type interferon-beta to have the activity of interferon-beta.

The antibody includes a monoclonal antibody, a polyclonal antibody, a multispecific antibody (e.g., bispecific antibody) and a fragment thereof. A complete antibody is generally Y-shaped and consists of two long heavy chains H and two short light chains L. Each heavy chain and light chain are linked to each other by sulfide bonds, and are divided into a variable region V, a region that reacts with an antigen, and a constant region C, a region that expresses a function of effect. In the variable region, there is a complementarity-determining region (CDR) that determines a structure of the variable region so as to form specific binding to an antigen and controls an antibody binding strength. The fragments of the antibody represent specific sites capable of reacting with an antigen to exhibit antigen-binding activity, and may include, for example, a Fab fragment (fragment by papain digestion), a Fab' fragment (fragment by pepsin digestion and partial reduction), a F(ab')2 fragment (fragment by pepsin digestion), a Facb (fragment by plasmin digestion), a Fd (fragment by pepsin digestion, partial reduction and reaggregation), a scFv fragment (fragment by molecular biology technique), and the like. Preferably, the antibody is an antibody or a fragment thereof that recognizes a tumor-specific antigen, and may be used as a target therapeutic agent for cancer. For example, the target therapeutic agent may be Trastuzumab, an antibody therapeutic agent that targets a human epidermal growth factor receptor (HER-2), and Cetuximab, an antibody therapeutic agent that targets an epidermal growth factor receptor (EGFR), Atezolizumab, an antibody therapeutic agent that targets PD-L1 expressed on the surface of cancer cells, and the like. In this case, Trastuzumab may consist of a heavy chain having an amino acid sequence defined by SEQ ID NO: 3 and a light chain having an amino acid sequence defined by SEQ ID NO: 4, Cetuximab may consist of a heavy chain having an amino acid sequence defined by SEQ ID NO: 5 and a light chain having an amino acid sequence defined by SEQ ID NO: 6, and Atezolizumab may consist of a heavy chain having an amino acid sequence defined by SEQ ID NO: 7 and a light chain having an amino acid sequence defined by SEQ ID NO: 8.

The recombinant protein may be a fusion or complex formed by linking the interferon-beta mutein and the antibody or the fragment thereof by a peptide linker. The peptide linker refers to a molecule serving to link two or more separate materials to each other, as a short-fragmented amino acid or amino acid analog in which two or more amino acids or amino acids-like materials are linked to each other by peptide bonds. In this case, glycine, serine, alanine, etc. are used as major constituent amino acids, so that a glycine-serine linker, a glycine-serine-alanine linker, etc. may be used. Such a linker may be linked to a heavy chain C-terminus of the antibody or a light chain C-terminus of the antibody, or a light chain C-terminus and a heavy chain C-terminus of the antibody may be linked to an N-terminus of the linker. In this case, the N-terminus of the interferon beta mutein may be linked to the C-terminus of the linker.

According to another exemplary embodiment of the present invention, there is provided a polynucleotide encoding the recombinant protein.

The polynucleotide is a high molecular compound in which nucleotides as chemical monomers consisting of three elements of a base, sugar, and phosphoric acid, are linked in a chain form through a plurality of phosphate ester bonds, and a polymer of deoxyribonucleotides or ribonucleotides that exist in single-stranded or double-stranded form.

The polynucleotide may be an RNA genome sequence, DNA (gDNA or cDNA), and an RNA sequence transcribed therefrom, and includes not only a nucleotide sequence encoding the amino acid sequence of the recombinant protein but also a sequence complementary to the sequence. Preferably, the polynucleotide may be a nucleotide sequence defined by SEQ ID NO: 9 encoding a recombinant protein in which the interferon-beta mutein and the heavy chain of Trastuzumab are linked, a nucleotide sequence defined by SEQ ID NO: 10 encoding a recombinant protein in which the interferon-beta mutein and the heavy chain of Cetuximab are linked, or a nucleotide sequence defined by SEQ ID NO: 11 encoding a recombinant protein in which the interferon-beta mutein and the heavy chain of Atezolizumab are linked.

According to another exemplary embodiment of the present invention, there is provided an expression vector comprising the polynucleotide.

The expression vector is a vector capable of expressing the recombinant protein comprising the interferon-beta mutein and the antibody or the fragment thereof in a host cell, and refers to a gene construct comprising a gene sequence and an expression regulatory sequence operably linked so that a gene insert is expressed. The "operably linked" means that a nucleic acid sequence encoding a target protein is functionally linked to a nucleic acid expression regulatory sequence to perform a general function. The "expression regulatory sequence" refers to a DNA sequence that regulates the expression of an operably linked polynucleotide sequence in a specific host cell. Such an expression vector may be prepared using a genetic recombination technique well-known in the art, and enzymes commonly used in the art for site-specific DNA cleavage and linkage may be used.

The expression vector includes a signal sequence or a leader sequence for membrane targeting or secretion in addition to expression regulatory elements, such as a promoter, an operator, an initiation codon, a termination codon, a polyadenylation signal, and an enhancer, and may be variously prepared according to a purpose. In addition, the expression vector contains a selection marker for selecting a host cell containing the expression vector, and a replicable expression vector may self-replicate comprising a replication origin, or be integrated into host DNA. The expression vector may use, without limitation, any vector that can be conventionally used for expression of an external gene in the art, and may be, for example, a plasmid vector, a cosmid vector, a viral vector, and the like.

According to yet another exemplary embodiment of the present invention, there is provided a host cell transformed with the expression vector.

The host cell may be selected to regulate the expression of an inserted sequence or proceed with a gene product in a preferred specific manner. Different host cells have characteristic and specific mechanisms for translation of the protein and processing and modification after translation.

A suitable cell line or host system may be selected to provide preferable modification and processing of expressed heterogeneous proteins. The expression in yeast may produce biological active products. The expression in eukaryotes may increase a folding possibility of peptide chains constituting the polypeptide or protein.

The host cell may use, without limitation, any host cell known in the art capable of cloning and expressing the vector stably and continuously, and may include, for example, *E. coli*, such as *E. coli* JM109, *E. coli* BL21DE, *E. coli* DH5, *E. coli* RR1, *E. coli* LE392, *E. coli* B, *E. coli* X 1776, and *E. coli* W3110, *Agrobacterium* genus strains such as *Agrobacterium* A4, *Bacilli* such as *Bacillus subtilis*, intestinal bacteria such as *Salmonella typhimurium* and *Serratia marcescens*, various *Pseudomonas* genus strains, and the like. In addition, in the case of transfection of the expression vector into eukaryotes, as the host cell, yeast (*Saccharomyces cerevisiae*), insect cells, human cells (e.g., Chinese hamster ovary (CHO), W138, BHK, COS-7, 293, HepG2, 3T3, RIN, MDCK cell lines), and the like may be used.

The introduction of the expression vector may be performed using a transformation method commonly available in the art. The "transformation" refers to a phenomenon in which DNA causes an artificially genetic change so as to be replicable as a factor of a chromosome in the host cell or by chromosomal integration completion by introducing foreign DNA into a host cell. The transformation method includes a $CaCl_2$ precipitation method, a Hanahan method for enhancing efficiency by using a reduced material, dimethyl sulfoxide (DMSO) in the $CaCl_2$ method, an electroporation method, a calcium phosphate precipitation method, a protoplast fusion method, a stirring method using silicon carbide fiber, a bacterium *agrobacterium*-mediated transformation method, a transformation method using PEG, dextran sulfate, lipofectamine, and drying/inhibition-mediated transformation methods, and the like.

Further, according to another exemplary embodiment of the present invention, there is provided a pharmaceutical composition for treating cancer comprising the recombinant protein as an active ingredient.

The recombinant protein has a structure in which an interferon-beta mutein with improved physical properties and an antibody or a fragment thereof are linked, and it has been confirmed that the recombinant protein has excellent purification efficiency and biological activity, and has immunomodulatory efficacy, anticancer efficacy, ADCC efficacy, and the like on various cancer cell lines. Accordingly, the composition containing such the recombinant protein as the active ingredient exhibits an effect of inhibiting the proliferation and activity of cancer cells, and can be used as a pharmaceutical composition for treating cancer.

In the formulation method of the composition, a pharmaceutical formulation may be prepared by mixing commonly used excipients, adjuvants, analgesic agents, isotonic agents, preservatives, and other pharmaceutically acceptable adjuvants, and formulating a conventional pharmaceutically acceptable formulation. The formulation may be oral formulations, such as powders, granules, tablets, capsules, suspensions, emulsions, syrups, and aerosols, or external preparations, suppositories, and sterile injection solutions. Solid formulations for oral administration may include tablets, pills, powders, granules, capsules, and the like, and liquid formulations for oral administration include suspensions, internal solutions, emulsions, syrups, and the like. Formulations for parenteral administration include a sterile aqueous solution, a non-aqueous solution, a suspension, an emulsion, a lyophilizing agent, and a suppository.

The method of administering the composition varies according to the condition and weight of a patient, the degree of a disease, a drug form, and route and period of administration, but may be properly selected by those skilled in the art. However, for a preferable effect, the composition may be administered at 0.001 to 1,000 mg/kg per day. The composition may be administered once a day or several times a day. The route of administration can be performed by all methods, and for example, the composition may be administered by oral, rectal or intravenous, intramuscular, subcutaneous, intrauterine dural or cerebrovascular injection.

In addition, in the present invention, in the production and isolation/purification of a R27T mutein of interferon beta, it was confirmed that C17 of interferon-beta, that is, cysteine as an amino acid at position 17, plays an important role in the stability of the mutein. As a result, when the amino acid at position 17 is modified with another amino acid, the modification affects the stability during production, isolation, purification, and further storage and distribution.

Therefore, the present invention provides a method for increasing protein stability during production or isolation and purification of the recombinant protein, the method comprising:

(a) culturing a host cell transformed to express a recombinant protein comprising an antibody or a fragment thereof directly or indirectly covalently bound to an interferon-beta mutein; and (b) isolating and purifying the recombinant protein comprising the antibody or the fragment thereof directly or indirectly covalently bound to the interferon-beta mutein from the cultured host cell or a culture product thereof, wherein in the preparing of the recombinant protein comprising the antibody or the fragment thereof directly or indirectly covalently bound to the interferon-beta mutein, the host cell is transformed to express the recombinant protein in which an amino acid at position 17, cysteine of the interferon-beta mutein is modified to another amino acid.

In the method of the present invention, the interferon-beta mutein is an R27T mutein of interferon-beta, and since C17 is additionally modified with another amino acid, the interferon-beta mutein expresses a recombinant protein comprising an antibody or a fragment thereof directly or indirectly covalently bound to a double mutein of C17N and R27T. In this case, N represents any amino acid except cysteine.

Preferably, the another amino acid to be modified may be serine.

In addition, a host cell expressing the recombinant protein comprising the antibody or the fragment thereof directly or indirectly covalently bound to the mutein may be a mammalian cell used for protein expression. Preferably, a Chinese hamster ovary (CHO) cell line, W138, BHK, COS-7, 293, HepG2, 3T3, RIN and MDCK cell lines may be used, and most preferably, the host cell in the present invention may be a CHO cell line.

Further, the present invention also provides the use of the recombinant protein for preparing an anticancer agent.

Further, the present invention provides a method for treating cancer comprising administering an effective amount of the composition comprising the recombinant protein to a subject in need thereof.

The term ‘effective amount’ of the present invention means an amount that exhibits effects of improving, treating, preventing, detecting, and diagnosing of cancer, or inhibiting or alleviating the disease when administered to the subject. The ‘subject’ may be animals, preferably, mammals, particularly animals comprising humans, and may also be cells, tissues, organs, and the like derived from animals. The subject may be a patient requiring the effects.

The ‘treatment’ of the present invention comprehensively refers to improving cancer or symptoms of cancer, and may include treating or substantially preventing the disease, or improving the conditions thereof and includes palliating, treating or preventing a symptom or most of symptoms derived from cancer, but is not limited thereto.

The term ‘comprising’ as used herein is used in the same meaning as ‘including’ or ‘characterized by’, and does not exclude additional ingredients or steps of the method which are not specifically mentioned in the composition or the method according to the present invention. The term ‘consisting of’ means excluding additional elements, steps or ingredients, etc., unless otherwise described. The term ‘essentially consisting of’ means including materials or steps which do not substantially affect basic properties thereof in addition to the described materials or steps within the range of the composition or the method.

Advantageous Effects

According to the present invention, the recombinant protein in which the interferon-beta mutein and the antibody or the fragment thereof are linked may improve the physical properties of interferon-beta through site-specific mutation, thereby improving biological activity and purification efficiency, and increasing the productivity thereof. Since both the function of interferon-beta and the characteristics of an antibody binding to a specific antigen are expressed, the recombinant protein can be usefully used as a targeted therapeutic agent for cancer and the like.

DESCRIPTION OF DRAWINGS

FIG. 2A is a graph showing the purification efficiency of Trastuzumab-IFNβ, Trastuzumab-IFNβ-R27T and Trastuzumab-IFNβ-C17S-R270T for each experiment. FIG. 2B is a graph of comparing average yields of repeated purification experiments of Trastuzumab-IFNβ, Trastuzumab-IFNβ-R27T and Trastuzumab-IFNβ-C17S-R270T. FIG. 2C is a graph of comparing the purification efficiency of Cetuximab-IFNβ-R27T and Cetuximab-IFNβ-C17S-R27T. FIG. 2D is a graph of comparing the purification efficiency of Atezolizumab-IFNβ-R27T and Atezolizumab-IFNβ-C17S-R27T.

FIG. 3A is a result of comparing protein aggregation of Trastuzumab-IFNβ, Trastuzumab-IFNβ-R27T and Trastuzumab-IFNβ-C17S-R270T. FIG. 3B is a result of comparing protein aggregation of Cetuximab-IFNβ-R27T and Cetuximab-IFNβ-C17S-R27T. FIG. 3C is a result of comparing protein aggregation of Atezolizumab-IFNβ-R27T and Atezolizumab-IFNβ-C17S-R27T.

MODES FOR THE INVENTION

Figure 1:
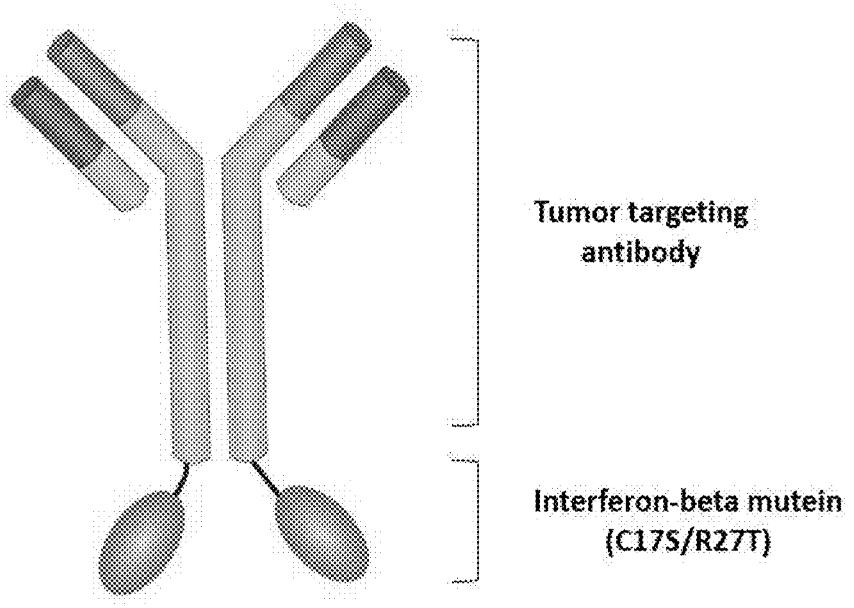
FIG. 1 is a schematic diagram illustrating a structure of a fusion protein in which an interferon-beta mutein and a tumor targeting antibody are linked.
Figure 2A:
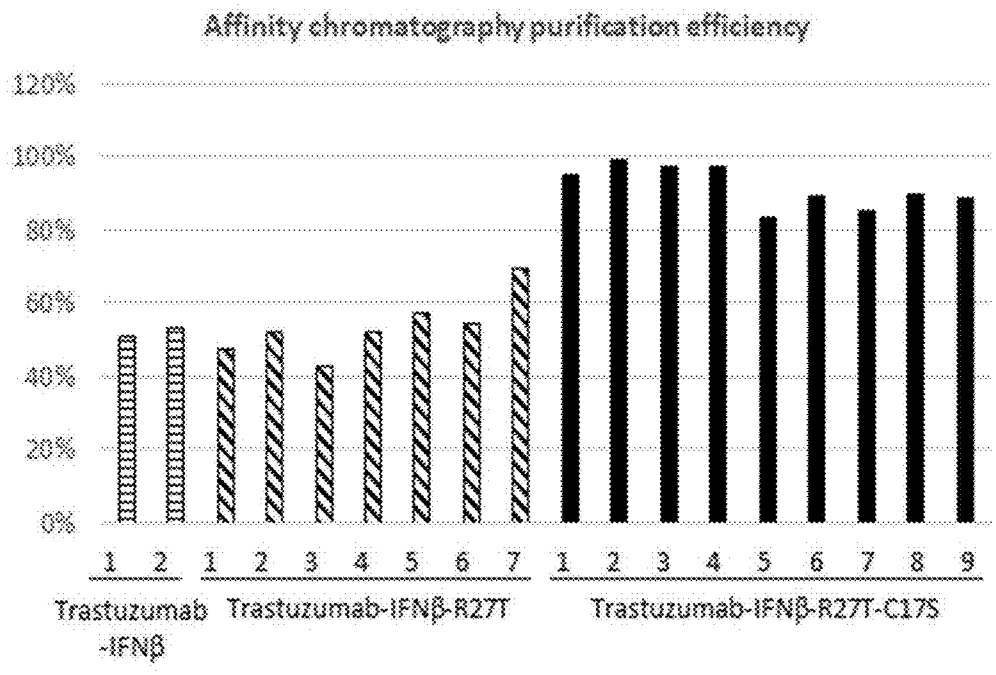
FIGS. 2A to 2D are results of comparing the purification efficiency of an antibody-interferon-beta mutein fusion protein during an affinity chromatography purification process.
Figure 2B:
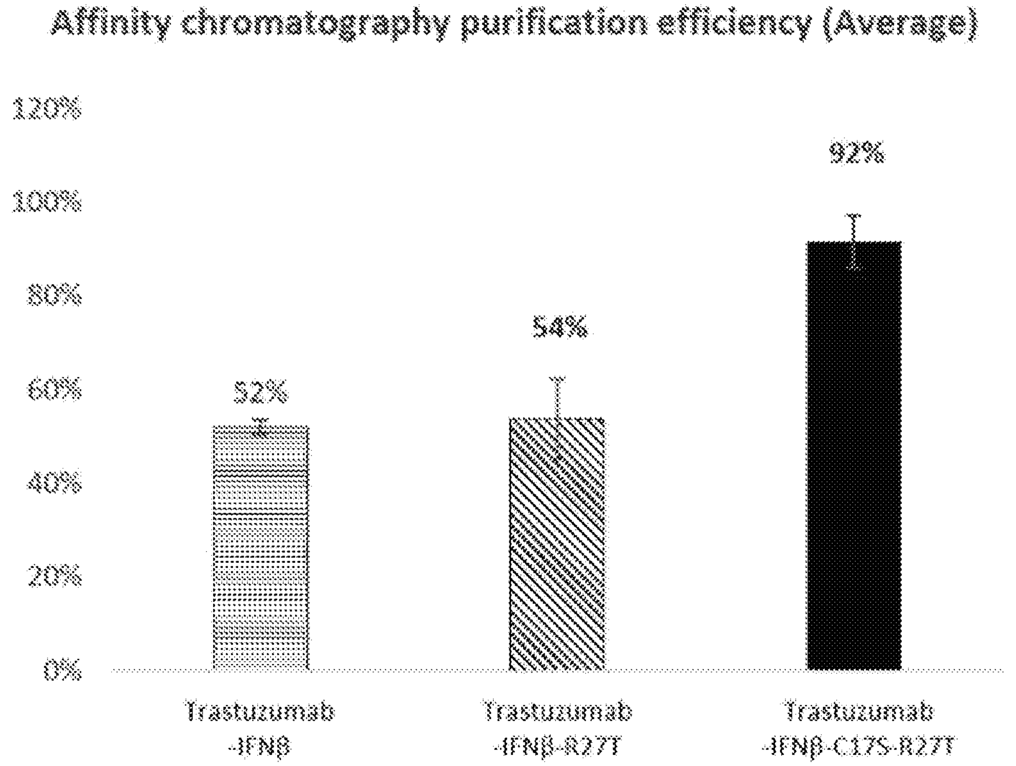
Figure 2C:
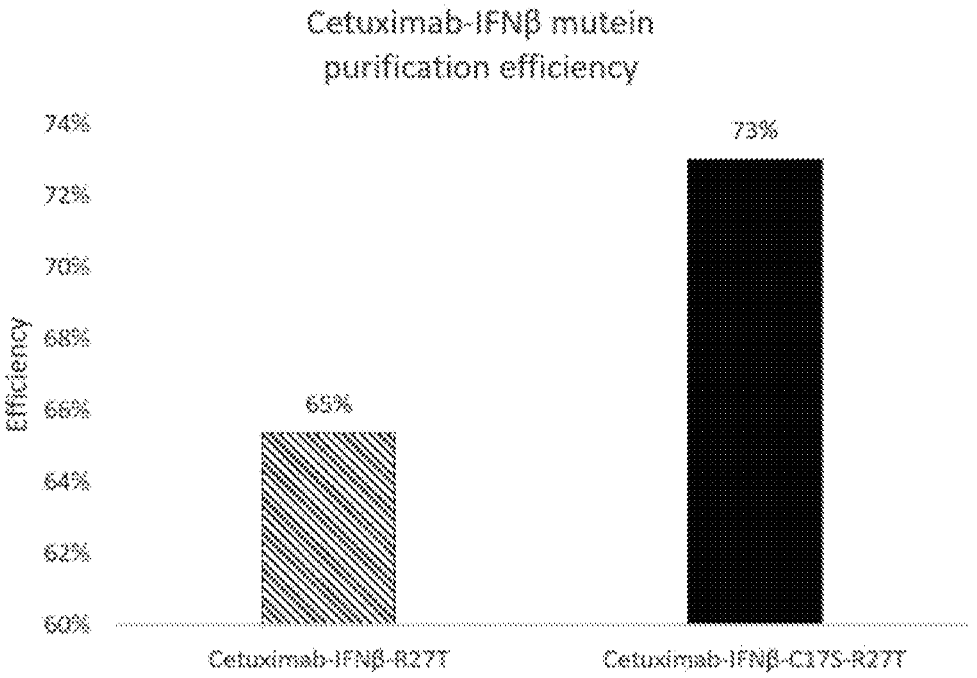
Figure 2D:
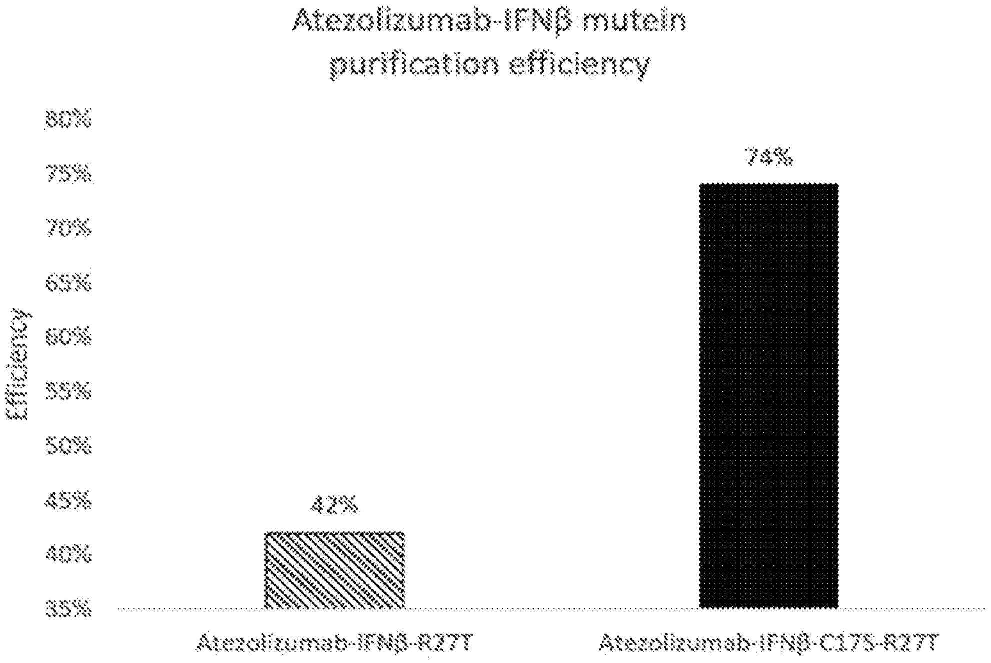

Hereinafter, the present invention will be described in more detail with reference to the accompanying drawings. However, the descriptions are just illustrative to help the understanding of the present invention, and the scope of the present invention is not limited by these illustrative descriptions.

1. Materials and Methods 1-1. Preparation Design of Fusion Protein

To establish a cell line transiently or stably expressing an antibody binding to an interferon-beta mutein, pCHO 1.0 (Life Technologies) was used as an expression vector. Trastuzumab, Cetuximab, and Atezolizumab were used as the antibody, and interferon-beta (IFN-β) used a mutein IFNβ-R27T in which an amino acid residue at position 27 was substituted with threonine or a mutein IFNβ-C17S-R27T in which an amino acid residue at position 27 1 was substituted with serine in addition to R27T.

A linker and the interferon-beta mutein R27T or C17S-R27T were cloned to bind to a heavy chain region of the antibody. Thereafter, restriction enzyme AvrII (CCTAGG) cleavage site and Bstz17I (GTATAC) cleavage site (Thermo Scientific, USA) were inserted into 3' and 5' terminuses of the entire gene, respectively, to secure a final gene of the heavy chain. In addition, restriction enzyme EcoRV (GATATC) cleavage site and PacI (TTAATTAA) were inserted into 3' and 5' terminuses of a light chain of the antibody to secure a final gene of the light chain. The final genes of the heavy and light chains were inserted into the pCHO 1.0 vector.

1-2. Expression of Fusion Protein Construct in Mammalian Cells

Expression vectors of Trastuzumab, Trastuzumab-interferon-beta-R27T (Trastuzumab-IFNβ-R27T) and Trastuzumab-interferon-beta-C17S-R27T (Trastuzumab-IFNβ-C17S-R27T) were transduced into CHO-S cells (Thermo Scientific) using a FreeStyle™ MAX reagent (Thermo Scientific). Cetuximab and Atezolizumab antibodies were also transduced in the same manner. A mixture obtained by adding OptiPRO™ SFM (Thermo Scientific) to a FreeStyle™ MAX reagent-DNA complex was put in CHO-S in a flask, and cultured in a humidified 8% $CO_2$ atmospheric pressure condition. A cell line expressing the fusion protein was stably selected after 48 hours of transduction. Cells were sorted through secondary selection with 10 to 50 μg/mL of puromycin and 100 to 1,000 nM of MTX. The selected cells were cultured with glucose to express the fusion protein for 5 or 7 days at 37° C. under conditions of humidified 8% $CO_2$ atmospheric pressure and 130 rpm.

1-3. Purification of Fusion Protein

A fusion protein expressed in CHO-S cells was purified by affinity chromatography. The CHO-S culture solution passed through a column filled with protein A Mabselect sure (Cytiva) and then purified by sequentially adding an equilibration buffer, a wash buffer, and an elution buffer to obtain the purified protein.

1-4. Protein Aggregation Assay

Aggregation analysis (FPLC-SEC) was performed to determine the physical properties. A filled size exclusion chromatography column, HiLoad (HiLoad 16/600 Superdex 200 pg), was connected to an AKTA purifier (Cytiva). After a maximum pressure was set to 0.3 Mpa, a sample purified by affinity chromatography was injected as much as 50% of a sample loop length by adjusting the concentration to 1 mg/mL. The aggregation rate of the protein was confirmed by confirming UV (280 nm) peaks.

1-5. Cell Lines and Culture Conditions

Human breast cancer cell lines MCF-7, MDA-MB-231, HCC-1954, and MDA-MB-453 and human gastric cancer cell lines SNU1, SNU620, Hs746T, and MKN45 were purchased from the Korean Cell Line Bank (KCLB, Seoul, South Korea). The human gastric cancer cell line NCI-N87 was purchased from the American Type Culture Collection (ATCC, Manassas, VA, USA). The U937 cell line (iLite type I IFN assay ready cell, ATCC #CRL1593.2) was purchased from Euro Diagnostica AB (Malmo, Sweden).

MCF-7, MDA-MB-231, HCC-1954, MDA-MB453, NCI-N87, SNU1, SNU620, Hs746T, MKN45 and U937 cell lines were cultured using a RPMI-1640 (HyClone, USA) medium containing 10% FBS (HyClone, USA), penicillin 100 units/mL and 100 μg/mL of streptomycin, and a Hs746T cell line was cultured using a DMEM (HyClone, USA) medium containing 10% FBS (HyClone, USA), penicillin 100 units/mL and 100 μg/mL of streptomycin. All of the cell lines were cultured at 37° C. under a humidified 5% $CO_2$ atmospheric pressure condition.

1-6. HER2 Recognition Ability Analysis with Flow Cytometry

The MCF-7, MDA-MB-231, and NCI-N87 cell lines were collected in EP tubes, respectively, and reacted with a blocking buffer at 4° C. for 1 hour, and washed twice with PBS. Thereafter, 1 μg of Trastuzumab, Trastuzumab-IFNβ-R27T and Trastuzumab-IFNβ-C17S-R27T were reacted and washed 3 times with PBS. Thereafter, a FITC-binding anti-human IgG secondary antibody was reacted and washed 3 times. Cells reacted with the antibody were analyzed using a CytoFlex (Beckman coulter, USA) flow cytometer.

1-7. Analysis of STAT1 Protein Phosphorylation by Western Blot

NCI-N87 cells were treated with IFN-β (5 to 200 pg/mL), IFNβ-C17S-R27T (5 to 200 pg/mL) or Trastuzumab-IFNβ-C17S-R27T (20 to 2,000 pg/mL) and then lysed using a RIPA lysis buffer (containing 150 mM NaCl, 1% Tryptone X-100, 1% sodium deoxycholate, 0.1% SDS, 50 mM Tris-HCl [pH 7.5], and 2 mM EDTA) added with a protease inhibitor mixture (Roche) and a phosphatase inhibitor mixture (Roche). The lysed cells were cultured at 4° C. for 20 minutes and centrifuged at 14,000 g for 10 minutes. A supernatant was recovered and the protein concentration was measured using a BCA protein assay kit (Thermo Scientific) according to the manufacturer's instructions. 20 μg of the protein was isolated by 10% SDS-PAGE and transferred to a polyvinyl difluoride (PVDF) membrane (BioRad). The PVDF membrane was blocked with a TBS-Tween20 buffer (containing 5% BSA) and cultured with a primary antibody overnight at 4° C. Thereafter, a secondary antibody was cultured for 1 hour at room temperature. The primary antibody used herein was anti-pSTAT1, anti-STAT1 (Cell Signaling Technology) or anti-β-actin (Santa Cruz Biotechnology), and the secondary antibody was anti-mouse IgG-HRP (ThermoFisher Scientific) or anti-rabbit IgG-HRP (ThermoFisher Scientific). HRP binding to the protein was visualized with a Clarity Western ECL substrate (Bio-Rad).

1-8. Measurement of Antibody-Dependent Cytotoxicity

A target cell HCC1954 or MDA-MB453 was treated with Control IgG (0.0001 to 100 nM), Trastuzumab (0.0001 to 100 nM), IFN-β (0.000001 to 1 nM), or Trastuzumab-IFNβ-C17S-R27T (0.0001 to 100 nM) and co-cultured with an effector cell to measure antibody-dependent cytotoxicity. As the effector cell, a natural killer cell (NK cell) cell line, NK-92MI-CD16a artificially overexpressing CD16a, was used to induce antibody-dependent cytotoxicity, and a ratio of the effector cell to the target cell (E:T ratio) was 8:1 and reacted with a drug for 4 hours. The cytotoxicity of the target cell was measured using a non-radioactive cytotoxicity assay (Promega, USA) that measured the release of lactate dehydrogenase (LDH) according to the manufacturer's instructions.

1-9. Measurement of Antiproliferative Activity

The antiproliferative activity was measured using a Water-Soluble Tetrazolium (WST) colorimetric assay (Ez-Cytox; Daeil Lab Service). NCI-N87, SNU1, SNU620, Hs746T and MKN45 cells were dispensed in a 96-well plate and treated with Trastuzumab, T-DM1, IFNβ-R27T, or Trastuzumab-IFNβ-C17S-R27T for each concentration (0.0001 to 100 nM) for 72 hours. Thereafter, 10 μl of WST was added to each well and cultured for 4 hours, and then the absorbance was measured at 450 nm using an absorbance meter (microplate reader, TECAN).

1-10. Measurement of Antiviral Activity

The antiviral activity of Trastuzumab-IFNβ, Trastuzumab-IFNβ-R27T and Trastuzumab-IFNβ-C17S-R27T was measured using a cytopathic effect assay (CPE assay). In order to measure the cytopathic effect, A549 cells were dispensed in a 96-well plate, and each drug was treated by concentration (0.78125 to 100 IU/mL). After 22 hours of drug treatment, EMCV of 1000 TCID50/mL was added. After co-culture for 22 hours, the cytopathic effect was measured from the absorbance values obtained using WST colorimetric assay.

1-11. Tumor Transition Experiment of Drug

A HER2-positive gastric cancer cell line, NCI-N87, was injected subcutaneously into 6-week-old female nude mice and xenografted. In order to track a drug, a fluorescent marker (CF750) was bound to a drug of IgG-IFNβ-R27T, Trastuzumab-IFNβ-R27T, IgG-IFNβ-C17S-R27T, or Trastuzumab-IFNβ-C17S-R27T. When the formed tumor size became about 100 $mm^3$, 3 mice were randomly allocated and administered with 100 μg/mice of IgG-IFNβ-R27T, Trastuzumab-IFNβ-R27T, IgG-IFNβ-C17S-R27T, or Trastuzumab-IFNβ-C17S-R27T. After 24 hours of drug administration, the mice were anesthetized and the vivo distribution of the drug was observed using a small animal optical in vivo imaging analyzer (Ami HTX, Spectral Instruments Imaging). In addition, for ex vivo analysis, cancer, liver, kidney, spleen, lung, and intestine were isolated from mice xenografted with cancer, and a drug distribution between tissues was observed. Experimental results were statistically processed through student T-test analysis.

1-12. Xenograft Animal Experiment

A HER2-positive breast cancer cell line, HCC1954, was injected subcutaneously into 5-week-old female nude mice. When the formed tumor size became about 100 $mm^3$, 5 mice were randomly allocated and administered with a vehicle and Trastuzumab-IFNβ-R27T or Trastuzumab-IFNβ-C17S-R27T 3 times a week for 3 weeks according to each dose (day 0). Tumors were measured twice a week using calipers, and calculated as (length×width$^2$)/2=volume ($mm^3$). The experimental results were statistically processed by two-way ANOVA analysis.

2. Results 2-1. Comparison of Purification Efficiency of Fusion Proteins

Cell lines expressing Trastuzumab-IFNβ-C17S-R27T, Trastuzumab-IFNβ-R27T, and Trastuzumab-IFNβ were expressed and purified under the same conditions. A transduced CHO-S cell line was cultured at 37° C. and 8% $CO_2$ for 5 days. The expression concentration of the fusion protein in the cell culture solution was measured using Cedex-bio (Roche), and then purified by affinity chromatography using an AKTA instrument system and protein A beads.

As a result, as shown in FIGS. 2A to 2D, the purification efficiency of Trastuzumab-IFNβ-C17S-R27T was about 92%, which was significantly improved as compared with Trastuzumab-IFNβ of 52% or Trastuzumab-IFNβ-R27T of 54%. Even when a Cetuximab antibody and an Atezolizumab antibody were applied, it was confirmed that the purification efficiency of the IFNβ-C17S-R27T-binding fusion protein was better.

2-2. Comparison of Protein Aggregation Rate of Fusion Protein

Since a protein aggregation problem was closely associated with the activity of materials and may cause immunogenicity in patients, the protein aggregation problem is an important part to be considered in the development of therapeutic agents. In order to analyze the protein aggregation, the purified fusion protein was comparatively analyzed by a FPLC-SEC method.

Figure 3A:
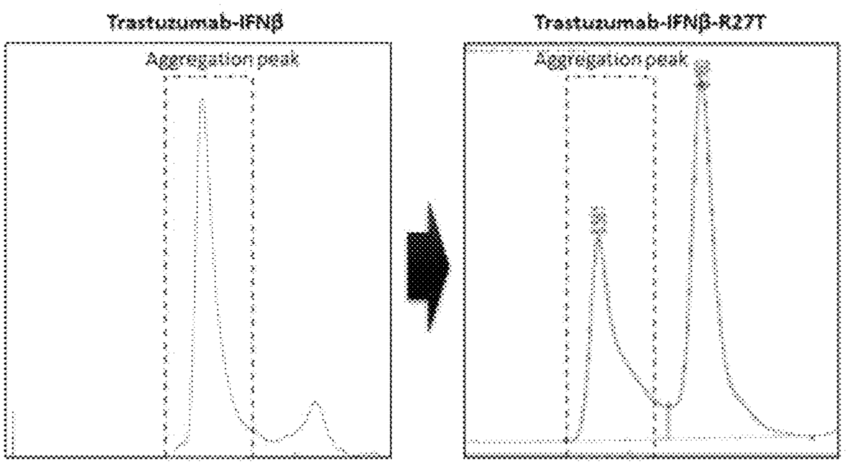
FIGS. 3A to 3C are results of comparing protein aggregation degrees of a purified antibody-interferon-beta mutein fusion protein analyzed by size exclusion chromatography.
Figure 3A:
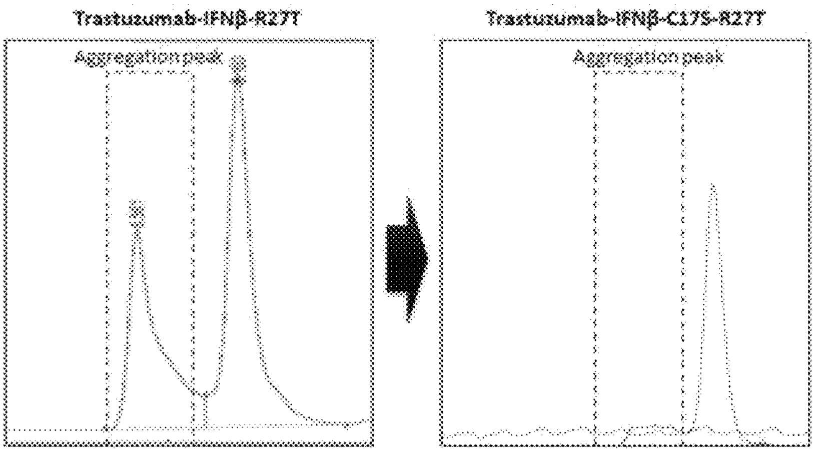
Figure 3B:
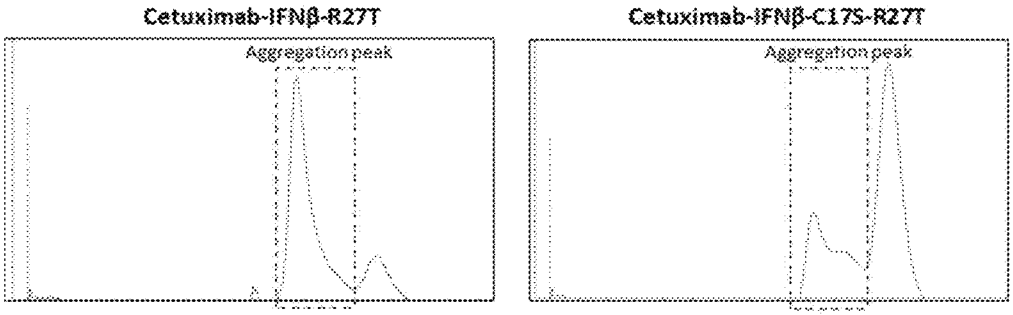
Figure 3C:
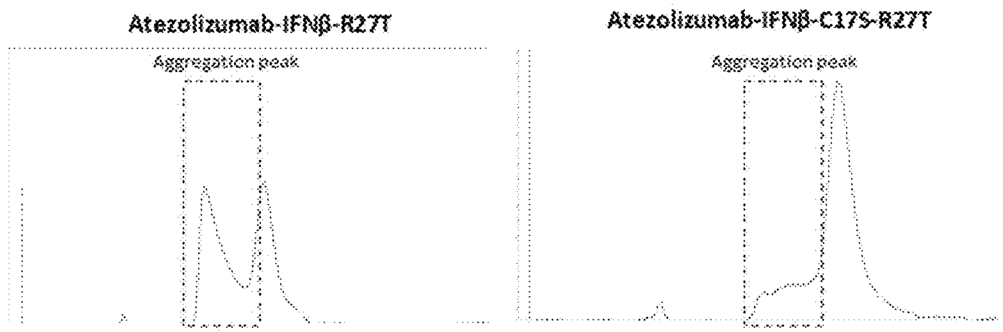

As a result, as shown in FIGS. 3A to 3C, it was confirmed that the protein aggregation rate of Trastuzumab-IFNβ-C17S-R27T was about 8%, which was significantly reduced compared to Trastuzumab-IFNβ-R27T of 40% or Trastuzumab-IFNβ of 85%. Even when a Cetuximab antibody and an Atezolizumab antibody were applied, it was confirmed that when the IFNβ-C17S-R27T was bound, the protein aggregation rate was significantly reduced.

2-3. Comparison of Cell Surface HER2 Antigen Recognition Ability of Trastuzumab-IFNβ-C17S-R27T The HER2 antigen recognition ability of Trastuzumab-IFNβ-C17S-R27T was compared with Trastuzumab-IFNβ-R27T and Trastuzumab. After each material reacted with NCI-N87 cells with high HER2 expression or MCF-7 or MDA-MB-231 cells with low HER2 expression, HER2 antigen recognition ability on the cell surface by shifting fluorescence intensity peaks was analyzed by using flow cytometry.

Figure 4A:
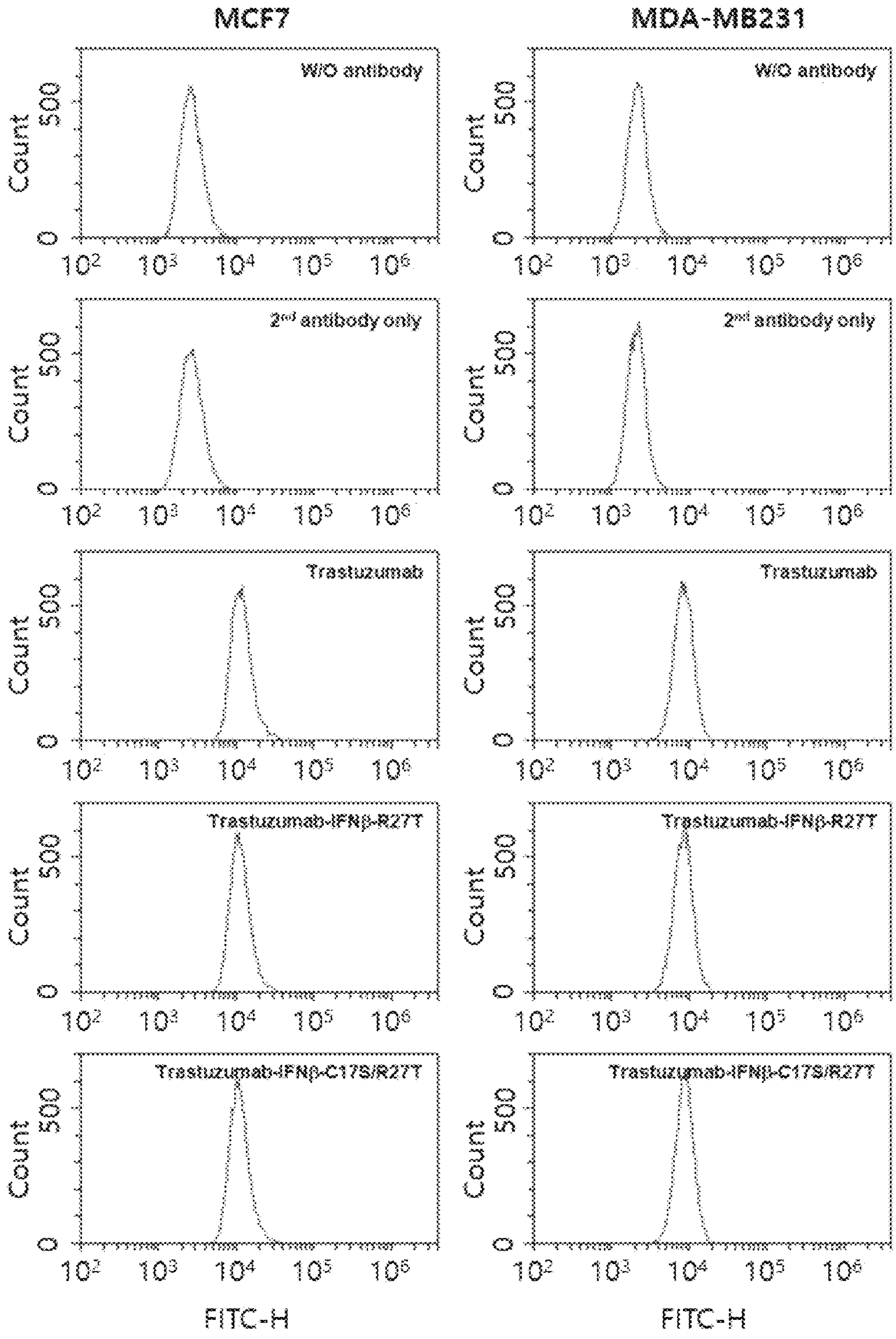
FIGS. 4A and 4B are results of analyzing HER2 binding ability of Trastuzumab, Trastuzumab-IFNβ-R27T and Trastuzumab-IFNβ-C17S-R27T by flow cytometry using three types of cell lines MCF-7, MDA-MB231, and NCI-N87.
Figure 4B:
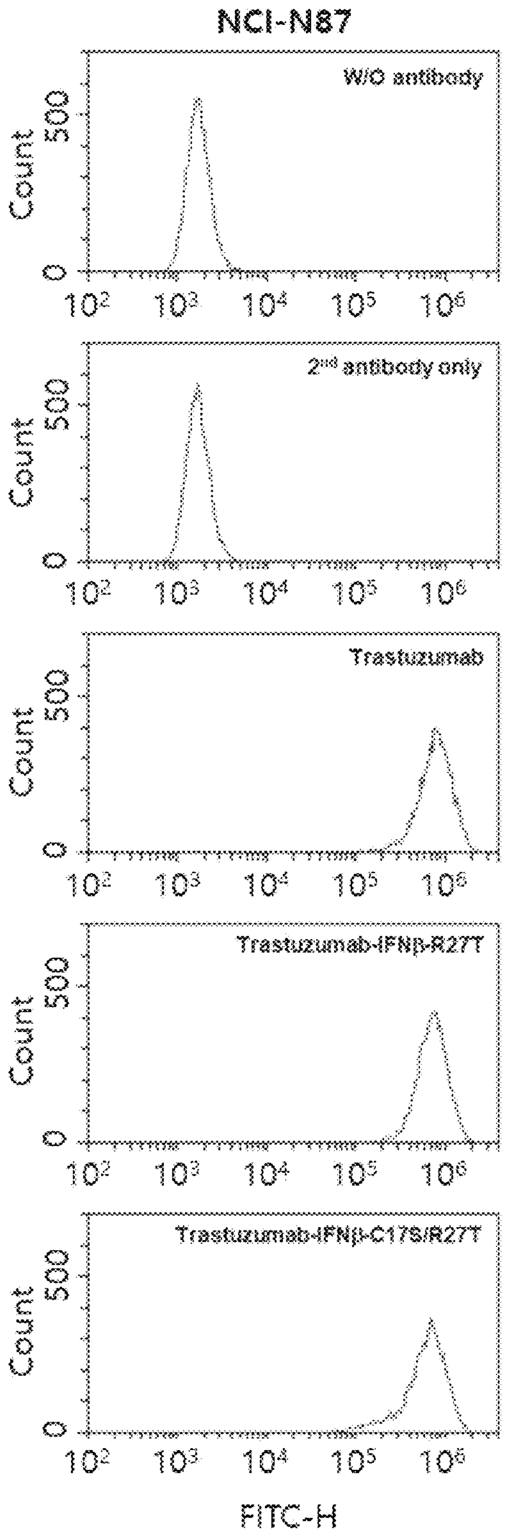

As a result, as shown in FIGS. 4A and 4B, in an untreated group as a control group, peaks were not shifted, whereas in groups treated with Trastuzumab, Trastuzumab-IFNβ-R27T, and Trastuzumab-IFNβ-C17S-R27T, fluorescence intensity peaks were shifted according to the degree of HER2 expression. In the MCF-7 and MDA-MB-231 cell lines with low HER2 expression, the fluorescence intensities of all the three materials were slightly increased, but the fluorescence intensity was greatly increased in the NCI-N87 cell line with high HER2 expression. In particular, it was confirmed that the HER2 antigen recognition ability of Trastuzumab-IFNβ-C17S-R27T was not different from that of Trastuzumab from the fact that there was no difference in the fluorescence peaks of the three materials.

2-4. IFN Biological Activity of Trastuzumab-IFNβ-C17S-R27T

Interferon activity occurred through a phosphorylation process of STAT, a lower signal transducer by binding to a type I IFN receptor. In order to confirm the interferon activity by Trastuzumab-IFNβ-C17S-R27T, NCI-N87 cells were treated with IFNβ-C17S-R27T and Trastuzumab-IFNβ-C17S-R27T at each concentration (0.004 to 40 pM) for 1 hour, and STAT1 phosphorylation and the expression of STAT1 and β-actin were confirmed through Western blotting.

Figure 5:
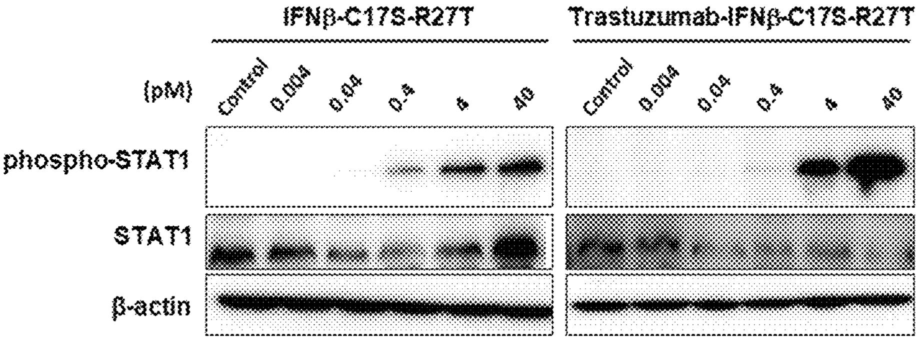
FIG. 5 is a result of analyzing the interferon signaling activity of Trastuzumab-IFNβ-C17S-R27T. This is a result of measuring the interferon-beta signaling activity by confirming a pSTAT1 expression level after one hour after treatment with IFNβ-C17S-R27T and Trastuzumab-IFNβ-C17S-R27T in a NCI-N87 cell line, respectively.

As a result, as shown in FIG. 5, it was shown that a signal of STAT1 phosphorylation was improved according to the treatment concentration of Trastuzumab-IFNβ-C17S-R27T, and the activity level of Trastuzumab-IFNβ-C17S-R27T was similar to that of IFNβ-C17S-R27T.

2-5. Antibody-Dependent Cytotoxicity of Trastuzumab-IFNβ-C17S-R27T

Antibody-dependent cytotoxicity was one of main anticancer mechanisms of Trastuzumab. When an antibody was bound to a target cell, cancer cell death occurred by activation of NK cells having an Fc gamma receptor capable of binding to an Fc domain of Trastuzumab.

Figure 6:
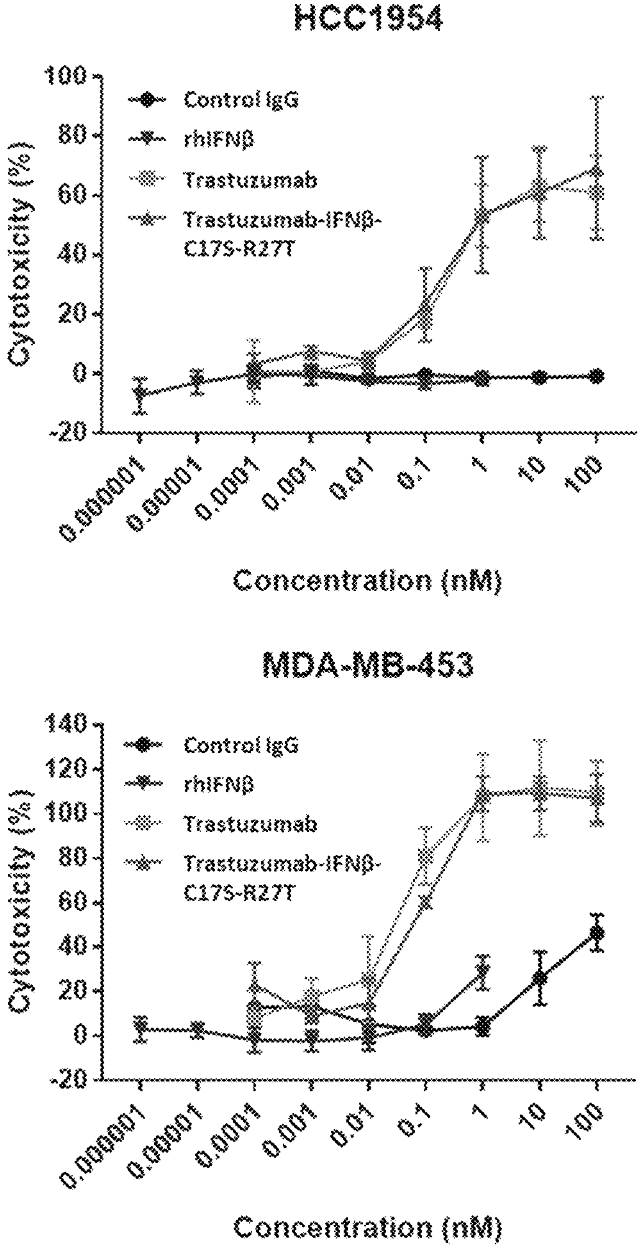
FIG. 6 is a result of comparative analysis of antibody-dependent cytotoxic effects of Control IgG, IFN-β, Trastuzumab, and Trastuzumab-IFNβ-C17S-R27T in HER2-positive cancer cell lines HCC1954 and MDA-MB453.

Since Trastuzumab-IFNβ-C17S-R27T includes Trastuzumab, Trastuzumab-IFNβ-C17S-R27T may include antibody-dependent cytotoxicity like Trastuzumab. Control IgG, Trastuzumab, IFN-β, and Trastuzumab-IFNβ-C17S-R27T were treated to a target cell, a HER2-positive cancer cell (HCC1954, MDA-MB453) by concentration, respectively, and an effector cell, an NK cell (NK-92MI-CD16a) was co-cultured at a ratio of the effector cell to the target cell of 8:1 to confirm the antibody-dependent cytotoxicity As a result, as shown in FIG. 6, Contol IgG and IFN-β hardly induced the antibody-dependent cytotoxicity, but Trastuzumab targeting HER2 and Trastuzumab-IFNβ-C17S-R27T containing Trastuzumab induced the same level of antibody-dependent cytotoxicity.

It was confirmed that the antibody-dependent cytotoxic effect induced by Trastuzumab was also fully maintained even in Trastuzumab-IFNβ-C17S-R27T.

2-6. HER2 Expression Level in Cancer Cells and Cancer Cell Proliferation Inhibitory Effect of Trastuzumab-IFNβ-C17S-R27T IFN-β had an effect of directly inhibiting the proliferation of cancer cells through receptor binding. The antiproliferative ability of Trastuzumab-IFNβ-C17S-R27T was evaluated in gastric cancer cell lines having various HER2 expression levels.

Figures 7A, 7B:
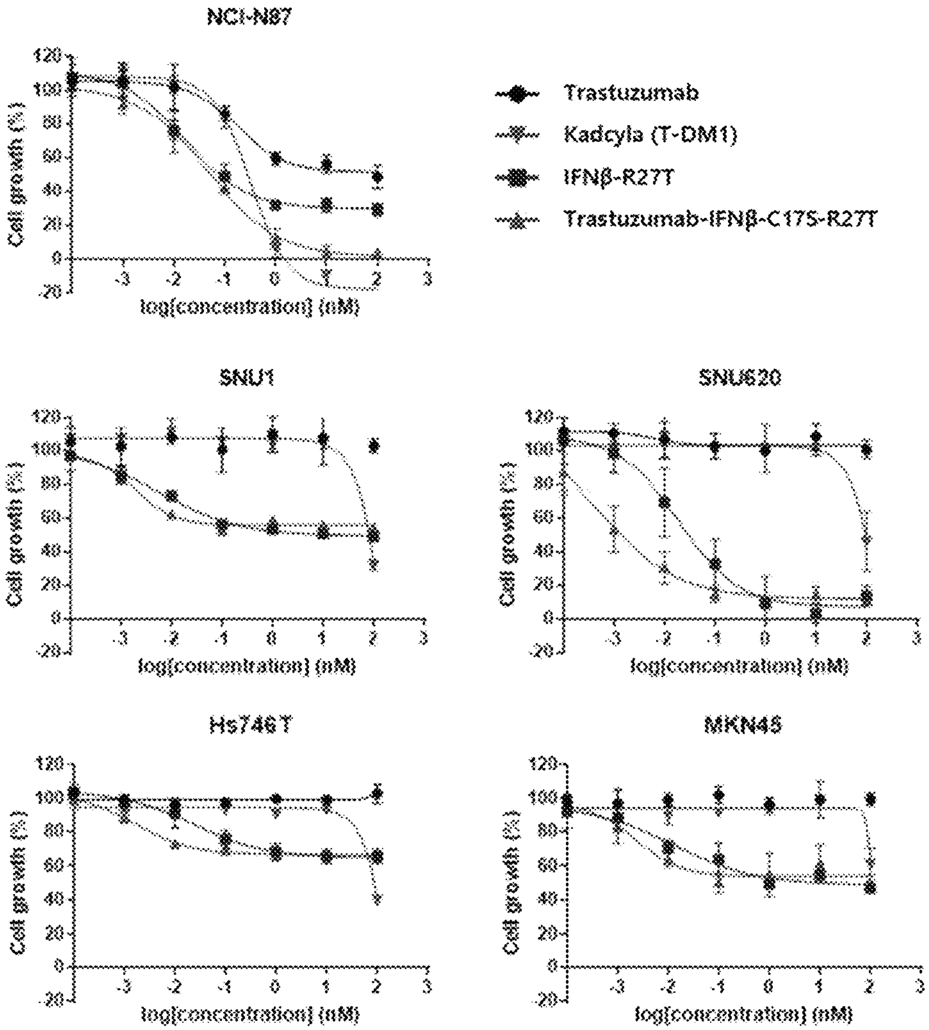
FIGS. 7A and 7B are results of comparing direct antiproliferative activity of each material of Trastuzumab, T-DM1, IFNβ-R27T, and Trastuzumab-IFNβ-C17S-R27T in a high HER2 expression cell line NCI-N87, medium HER2 expression cell lines SNU1 and SNU620, and low HER2 expression cell lines Hs746T and MKN45.

As a result, as shown in FIGS. 7A and 7B, Trastuzumab and a Trastuzumab-based antibody-drug conjugate, T-DM1 showed significant antiproliferative activity only in NCI-N87 cells with high HER2 expression. On the other hand, Trastuzumab-IFNβ-C17S-R27T observed significant antiproliferative activity not only in cell lines with high HER2 expression but also in gastric cancer cell lines with medium expression (SNU1, SNU620) and low expression (Hs746T, MKN45).

2-7. Antiviral Activity of Trastuzumab-IFNβ-C17S-R27T

When evaluating the activity of a material containing IFN, the most common assay method was measuring the antiviral activity that protected cells from a cytopathic effect (CPE) caused by a specific virus. Accordingly, the IFN activity of Trastuzumab-IFNβ, Trastuzumab-IFNβ-R27T and Trastuzumab-IFNβ-C17S-R27T was quantitatively measured and compared using CPE assay.

Figure 8A:
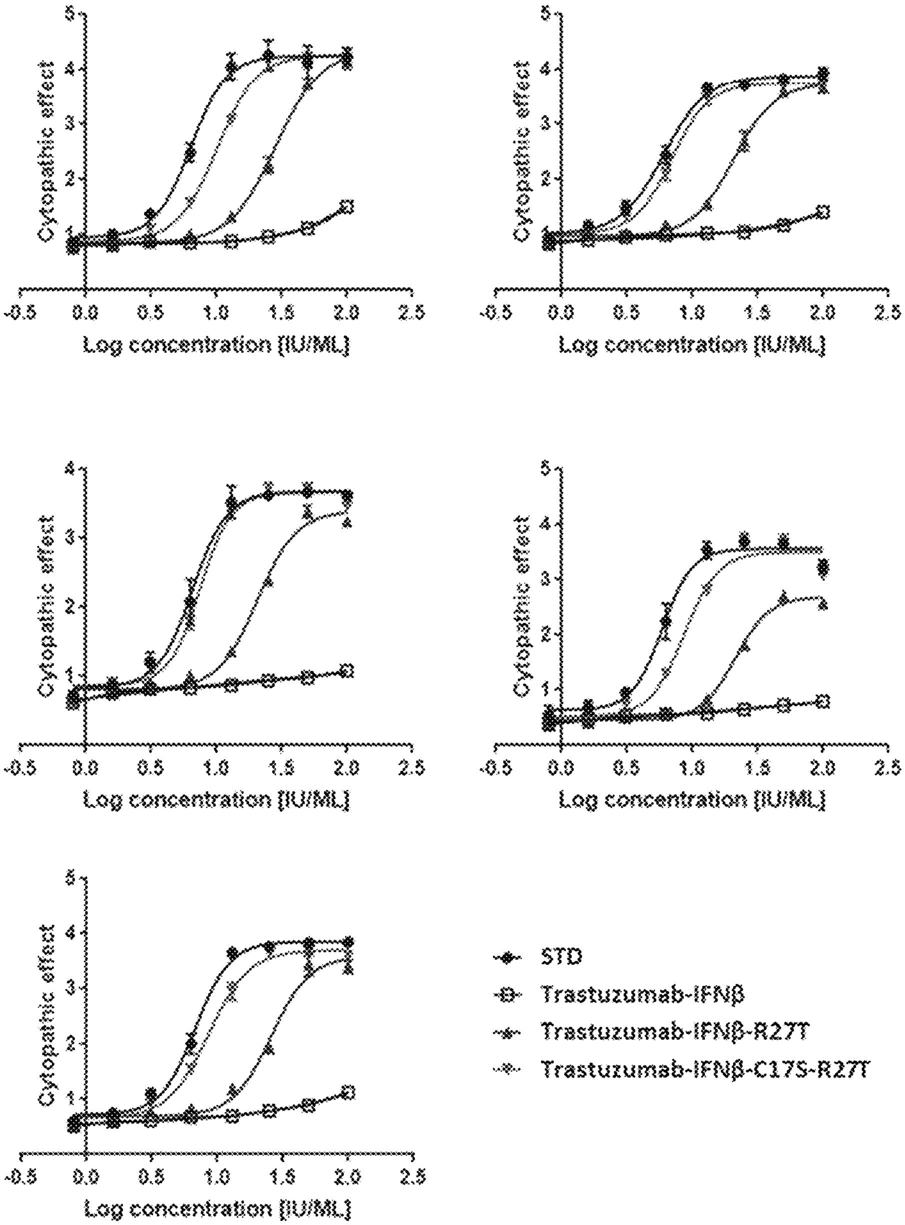
FIGS. 8A and 8B are results of quantitatively measuring and comparing the antiviral activity of Trastuzumab-IFNβ, Trastuzumab-IFNβ-R27T, and Trastuzumab-IFNβ-C17S-R27T through CPE assay.
Figures 8B, 9A:
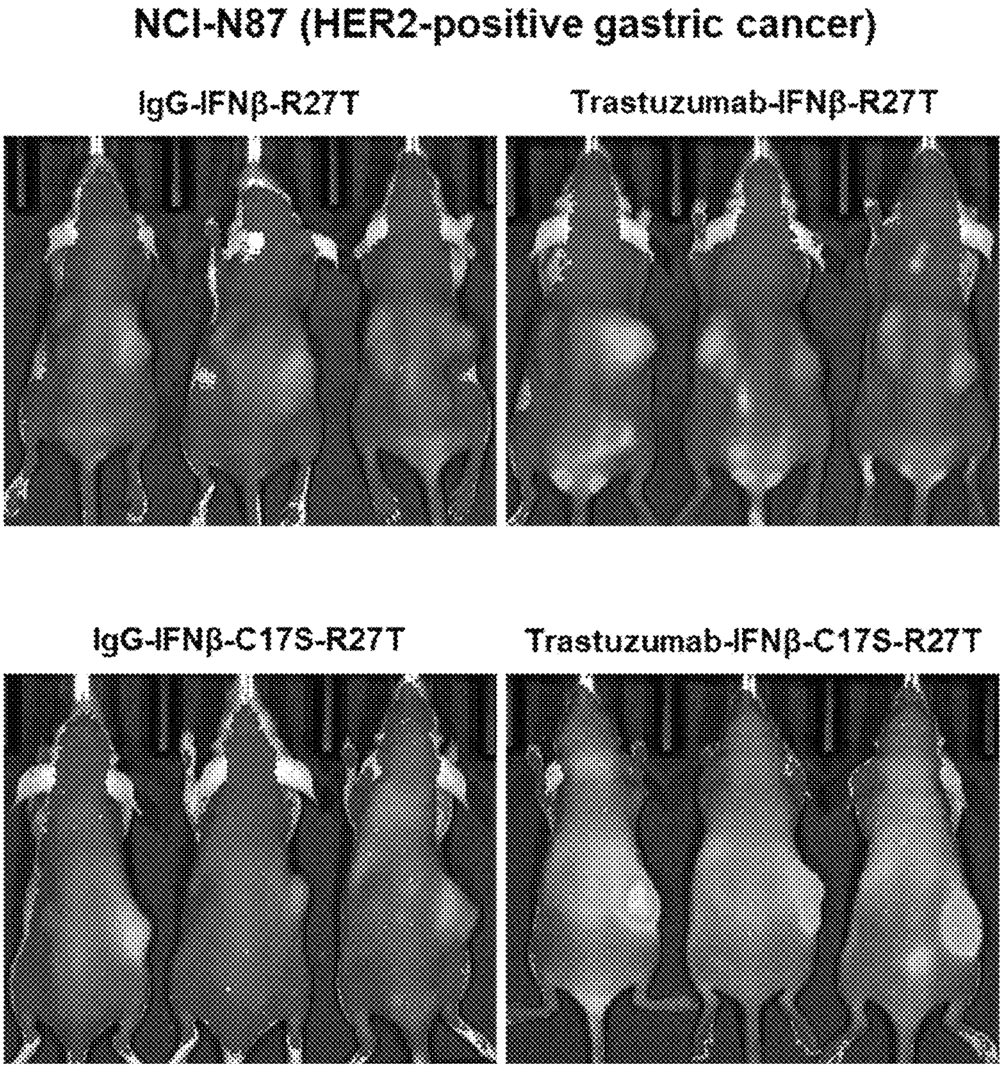
FIGS. 9A and 9B show the tumor targeting ability of Trastuzumab-IFNβ-C17S-R27T compared to Trastuzumab-IFNβ-R27T by xenografting NCI-N87 cells, a HER2-positive gastric cancer cell line, into nude mice.

As a result, as shown in FIGS. 8A and 8B, the antiviral activity effect of Trastuzumab-IFNβ-C17S-R27T was about 3 times higher than that of Trastuzumab-IFNβ-R27T, and Trastuzumab-IFNβ had almost no antiviral activity in a tested concentration range.

2-8. Tumor-Targeting Ability of Trastuzumab-IFNβ-C17S-R27T

In an animal model, the degree of tumor-specific movement of each fusion protein was compared and analyzed.

Figure 9B:
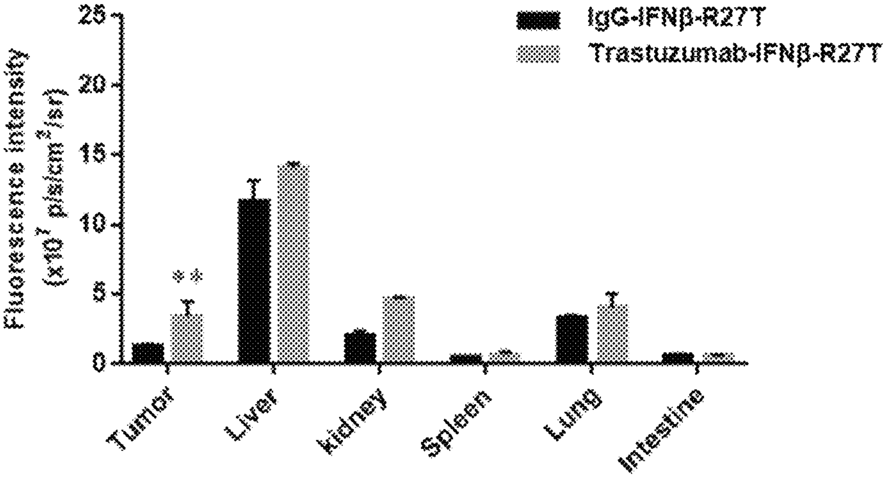
Figure 9B:
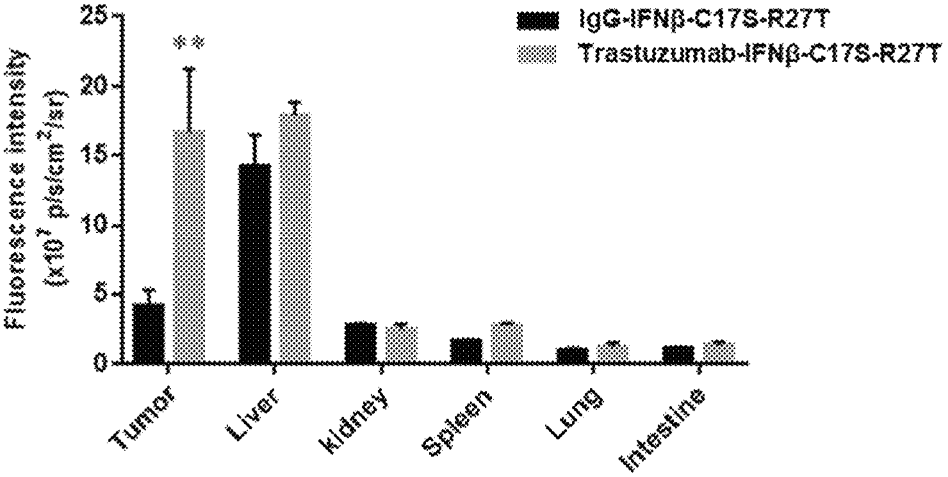

As a result, as shown in FIGS. 9A and 9B, a significant tumor targeting effect was observed in a Trastuzumab fusion protein group compared to an IgG fusion protein. In particular, Trastuzumab-IFNβ-R27T showed a tumor-targeting effect two times higher than IgG-IFNβ-R27T, whereas Trastuzumab-IFNβ-C17S-R27T showed a tumor-targeting effect at least four times higher than IgG-IFNβ-C17S-R27T. In addition, it was confirmed that the rate of transition to tumors of Trastuzumab-IFNβ-C17S-R27T compared to other organs was higher than that of Trastuzumab-IFNβ-R27T.

2-9. In Vivo Anticancer Effect of Trastuzumab-IFNβ-C17S-R27T

In order to confirm an anticancer effect of the fusion protein, a tumor xenograft model was constructed and then each material was administered, and the size of the tumor was measured.

Figure 10:
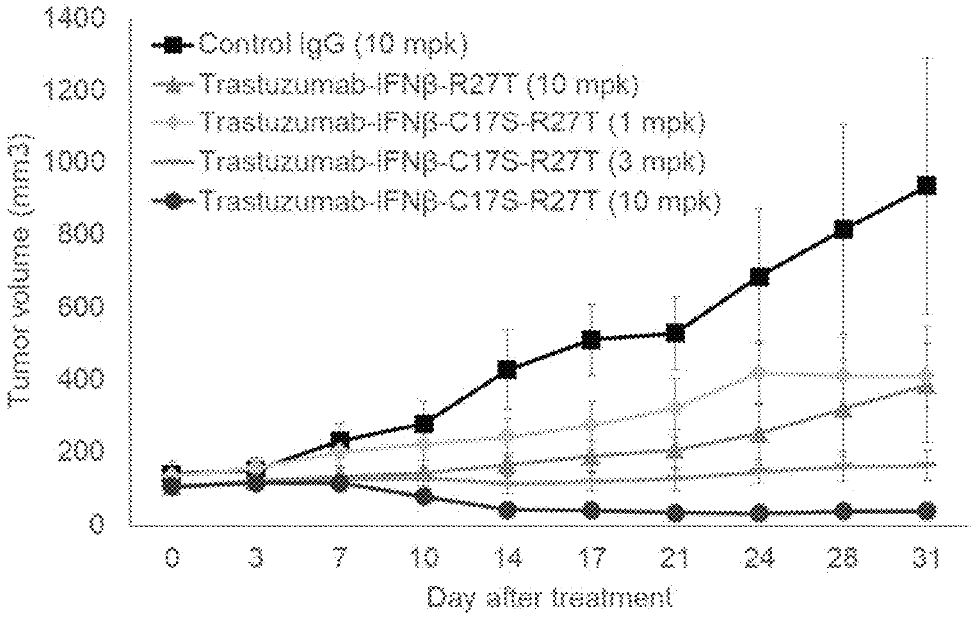
FIG. 10 shows the anticancer activity of Trastuzumab-IFNβ-C17S-R27T compared to Trastuzumab-IFNβ-R27T by xenografting HCC1954 cells, a HER2-positive breast cancer cell line, into nude mice. Trastuzumab-IFNβ-R27T was used at a single concentration of 10 mg/kg (mpk), and an effect of Trastuzumab-IFNβ-C17S-R27T was evaluated at three concentrations of 1, 3, and 10 mg/kg.

As a result, as shown in FIG. 10, in all groups treated with Trastuzumab-IFNβ-R27T at a concentration of 10 mpk or Trastuzumab-IFNβ-C17S-R27T at each concentration of 1, 3, and 10 mpk, a significant tumor inhibiting effect was observed compared to a vehicle. Trastuzumab-IFNβ-C17S-R27T concentration-dependently decreased a tumor volume, and complete remission (1/5) was observed in some mice at 10 mpk. In addition, it was confirmed that Trastuzumab-IFNβ-C17S-R27T had a better tumor inhibiting effect than Trastuzumab-IFNβ-R27T at the same concentration (10 mpk).

INDUSTRIAL APPLICABILITY

According to the present invention, a recombinant protein in which an interferon-beta mutein and an antibody or a fragment thereof are linked may improve the physical properties of interferon-beta through site-specific mutation, thereby improving biological activity and purification efficiency, and increasing the productivity thereof. Since both the function of interferon-beta and the characteristics of an antibody binding to a specific antigen are expressed, the recombinant protein can be usefully used as a targeted therapeutic agent for cancer and the like.

What is claimed is:

1. A recombinant protein comprising an interferon-beta mutein in which an amino acid residue at position 17 is substituted with serine and an amino acid residue at position 27 is substituted with threonine; and an antibody or an antigen-binding fragment thereof directly or indirectly covalently bound to the interferon-beta mutein, wherein the interferon-beta mutein comprises an amino acid sequence of SEQ ID NO: 1, wherein the antibody or antigen-binding fragment thereof specifically binds to an antigen that is expressed on a cancer cell.

2. The recombinant protein of claim 1, wherein the interferon-beta mutein includes glycosyl groups in amino acid residue at positions 80 and 25.

3. The recombinant protein of claim 1, wherein the antibody is at least one selected from the group consisting of Trastuzumab, Cetuximab, and Atezolizumab.

4. The recombinant protein of claim 1, wherein the interferon-beta mutein and the antibody or the antigen-binding fragment thereof are linked to each other by a peptide linker.

5. A polynucleotide encoding the recombinant protein of claim 1.

6. The polynucleotide of claim 5, wherein the polynucleotide is defined by a nucleotide sequence of SEQ ID NO: 9, 10 or 11.

7. An expression vector comprising the polynucleotide of claim 5.

8. A host cell transformed with the expression vector of claim 7.

9. A pharmaceutical composition comprising the recombinant protein of claim 1 as an active ingredient.

10. A method for increasing protein stability during production or isolation and purification of a recombinant protein, the method comprising:

(a) culturing a host cell transformed to express a recombinant protein comprising an antibody or an antigen-binding fragment thereof directly or indirectly covalently bound to an R27T mutein of interferon-beta; and (b) isolating and purifying the recombinant protein comprising the antibody or the antigen-binding fragment thereof directly or indirectly covalently bound to the interferon-beta mutein from the cultured host cell or a culture product thereof, wherein in the preparation of the recombinant protein comprising the antibody or the antigen-binding fragment thereof directly or indirectly covalently bound to the R27T mutein of interferon-beta, the host cell is transformed to express the recombinant protein in which an amino acid at position 17, cysteine of the interferon-beta mutein is modified to serine, wherein the interferon-beta mutein comprises an amino acid sequence of SEQ ID NO: 1, wherein the antibody or antigen-binding fragment thereof specifically binds to an antigen that is expressed on a cancer cell.

11. The method of claim 10, wherein the host cell is a mammalian cell.

12. A method for treating a cancer comprising administering an effective amount of a composition comprising the recombinant protein of claim 1 to a subject in need thereof, wherein the cancer expresses a target antigen, and wherein the antibody or antigen-binding fragment thereof of the recombinant protein specifically binds to the target antigen.

* * * * *

SEQUENCE LISTING

```
<160> NUMBER OF SEQ ID NOS: 11

<210> SEQ ID NO 1
<211> LENGTH: 166
<212> TYPE: PRT
<213> ORGANISM: Artificial Sequence
<220> FEATURE:
<223> OTHER INFORMATION: Amino acid sequence of interferon beta mutein

<400> SEQUENCE: 1

Met Ser Tyr Asn Leu Leu Gly Phe Leu Gln Arg Ser Ser Asn Phe Gln
1               5                   10                  15
```

```
Ser Gln Lys Leu Leu Trp Gln Leu Asn Gly Thr Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165


<210> SEQ ID NO 2
<211> LENGTH: 501
<212> TYPE: DNA
<213> ORGANISM: Artificial Sequence
<220> FEATURE:
<223> OTHER INFORMATION: Polynucleotide sequence of interferon beta
      mutein

<400> SEQUENCE: 2

atgtcctaca acctgctggg cttcctgcag cggtcctcca acttccagag ccagaaactg     60

ctgtggcagc tgaatggcac cctggaatac tgcctgaagg accggatgaa cttcgacatc    120

cccgaggaaa tcaagcagct gcagcagttc cagaaagagg acgccgctct gaccatctac    180

gagatgctgc agaacatctt cgccatcttc cggcaggact cctcctccac cggctggaac    240

gagacaatcg tggaaaatct gctggccaac gtgtaccacc agatcaacca cctgaaaacc    300

gtgctggaag agaagctgga aaaagaggac ttcacccggg gcaagctgat gtcctccctg    360

cacctgaagc ggtactacgg ccggatcctg cactacctga aggccaaaga atactcccac    420

tgcgcctgga ccatcgtgcg ggtggaaatc ctgcggaact tctactttat caaccggctg    480

accggctacc tgaggaactg a                                              501


<210> SEQ ID NO 3
<211> LENGTH: 450
<212> TYPE: PRT
<213> ORGANISM: Artificial Sequence
<220> FEATURE:
<223> OTHER INFORMATION: Amino acid sequence of Trastuzumab heavy chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

-continued

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

```
<210> SEQ ID NO 4
<211> LENGTH: 214
<212> TYPE: PRT
<213> ORGANISM: Artificial Sequence
<220> FEATURE:
<223> OTHER INFORMATION: Amino acid sequence of Trastuzumab light chain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 5
<211> LENGTH: 449
<212> TYPE: PRT
<213> ORGANISM: Artificial Sequence
<220> FEATURE:
<223> OTHER INFORMATION: Amino acid sequence of Cetuximab heavy chain

<400> SEQUENCE: 5

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95
```

-continued

```
Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 6
<211> LENGTH: 214
<212> TYPE: PRT
<213> ORGANISM: Artificial Sequence
<220> FEATURE:
<223> OTHER INFORMATION: Amino acid sequence of Cetuximab light chain

<400> SEQUENCE: 6

```
Asp Ile Leu Leu Thr Gln Ser Pro Val Ile Leu Ser Val Ser Pro Gly
```

```
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 448
<212> TYPE: PRT
<213> ORGANISM: Artificial Sequence
<220> FEATURE:
<223> OTHER INFORMATION: Amino acid sequence of Atezolizumab heavy chain

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

-continued 145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Ala Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 8
<211> LENGTH: 214
<212> TYPE: PRT
<213> ORGANISM: Artificial Sequence
<220> FEATURE:
<223> OTHER INFORMATION: Amino acid sequence of Atezolizumab light chain

<400> SEQUENCE: 8

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro

-continued

```
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 9
<211> LENGTH: 1896
<212> TYPE: DNA
<213> ORGANISM: Artificial Sequence
<220> FEATURE:
<223> OTHER INFORMATION: Polynucleotide sequence of Trastuzumab-
      interferon beta mutein heavy chain

<400> SEQUENCE: 9

gaggtgcagc tggtggaatc tggcggagga ctggtgcagc ctggcggctc tctgagactg     60

tcttgtgccg cctccggctt caacatcaag gacacctaca tccactgggt gcgacaggcc    120

cctggcaagg gactggaatg ggtggcccgg atctatccca ccaacggcta caccagatac    180

gccgactctg tgaagggccg gttcaccatc tccgccgaca cctccaagaa caccgcctac    240

ctgcagatga actccctgcg ggccgaggac accgccgtgt actactgctc tagatgggga    300

ggcgacggct tctacgccat ggactattgg ggccagggca ccctcgtgac cgtgtcctct    360

gcttctacca agggcccctc cgtgttccct ctggcccctt ccagcaagtc tacctctggc    420

ggcacagccg ctctgggctg cctcgtgaag gactacttcc ccgagcccgt gacagtgtct    480

tggaactctg gcgccctgac ctccggcgtg cacacctttc cagctgtgct gcagtccagc    540

ggcctgtact ccctgtcctc cgtcgtgact gtgccctcca gctctctggg cacccagacc    600

tacatctgca acgtgaacca caagccctcc aacaccaagg tggacaagaa ggtggaaccc    660

aagtcctgcg acaagaccca cacctgtccc ccttgtcctg cccctgaact gctgggcgga    720

cccagcgtgt tcctgttccc cccaaagcct aaggacaccc tgatgatctc ccggaccccc    780

gaagtgacct gcgtggtggt ggatgtgtcc cacgaggacc ctgaagtgaa gttcaattgg    840

tacgtggacg gcgtggaagt gcacaacgcc aagaccaagc ctagagagga acagtacaac    900

tccacctacc gggtggtgtc cgtgctgacc gtgctgcatc aggactggct gaacggcaaa    960

gagtacaagt gcaaggtgtc caacaaggcc ctgcctgccc ccatcgaaaa gaccatctcc   1020

aaggccaagg gccagccccg ggaaccccag gtgtacacac tgccccctag ccgggaagag   1080

atgaccaaga accaggtgtc cctgacctgt ctcgtgaaag gcttctaccc ctccgatatc   1140

gccgtggaat gggagtccaa cggccagcct gagaacaact acaagaccac cccccctgtg   1200
```

ctggactccg acggctcatt cttcctgtac agcaagctga cagtggacaa gtcccggtgg 1260
cagcagggca acgtgttctc ctgctccgtg atgcacgagg ccctgcacaa ccactacacc 1320
cagaagtccc tgtccctgtc tcccggaaaa ggcggaggcg gatctggcgg cggtggttca 1380
ggcggtggat ccggcatgtc ctacaacctg ctgggcttcc tgcagcggtc ctccaacttc 1440
cagtcccaga aactgctgtg gcagctgaat ggcaccctgg aatactgcct gaaggaccgg 1500
atgaacttcg acatccccga ggaaatcaag cagctgcagc agttccagaa agaggacgcc 1560
gctctgacca tctacgagat gctgcagaac atcttcgcca tcttccggca ggactcctcc 1620
tccaccggct ggaacgagac aatcgtggaa aatctgctgg ccaacgtgta ccaccagatc 1680
aaccacctga aaaccgtgct ggaagagaag ctggaaaaag aggacttcac ccggggcaag 1740
ctgatgtcct ccctgcacct gaagcggtac tacggccgga tcctgcacta cctgaaggcc 1800
aaagaatact cccactgcgc ctggaccatc gtgcgggtgg aaatcctgcg gaacttctac 1860
tttatcaacc ggctgaccgg ctacctgagg aactga 1896

<210> SEQ ID NO 10
<211> LENGTH: 1893
<212> TYPE: DNA
<213> ORGANISM: Artificial Sequence
<220> FEATURE:
<223> OTHER INFORMATION: Polynucleotide sequence of Cetuximab-interferon beta mutein heavy chain

<400> SEQUENCE: 10
caggtgcagc tgaagcagtc tggccctgga ctggtgcagc cttcccagtc cctgtccatc 60
acctgtaccg tgtccggctt ctccctgacc aactacggcg tgcactgggt gcgacagtct 120
ccaggcaagg gcctggaatg gctgggagtg atttggagcg gcggcaacac cgactacaac 180 accccctttca cctcccggct gagcatcaac aaggacaact ccaagtccca ggtgttcttc 240
aagatgaact ccctgcagtc caacgacacc gccatctact actgcgccag agccctgacc 300
tactatgact acgagttcgc ctactggggc cagggcaccc tcgtgacagt gtctgccgct 360
tctaccaagg gcccctccgt gtttcctctg gccccttcca gcaagtccac ctctggcgga 420
acagccgctc tgggctgcct cgtgaaggac tacttccccg agcccgtgac cgtgtcctgg 480
aattctggcg ctctgaccag cggagtgcac accttccctg ctgtgctgca gtcctccggc 540
ctgtactccc tgtcctccgt cgtgactgtg ccctccagct ctctgggcac ccagacctac 600
atctgcaacg tgaaccacaa gccctccaac accaaggtgg acaagaaggt ggaacccaag 660
tcctgcgaca agacccacac ctgtcccccct tgtcctgccc ctgaactgct gggcggacct 720
tccgtgttcc tgttcccccc aaagcccaag gacaccctga tgatctcccg gacccccgaa 780
gtgacctgcg tggtggtgga tgtgtcccac gaggaccctg aagtgaagtt caattggtac 840
gtggacggcg tggaagtgca caacgccaag accaagccta gagaggaaca gtacaactcc 900
acctaccggg tggtgtccgt gctgaccgtg ctgcatcagg actggctgaa cggcaaagag 960
tacaagtgca aggtgtccaa caaggccctg cctgccccca tcgaaaagac catctccaag 1020
gccaagggac agccccgcga gccccaggtg tacacactgc ctccatctcg ggacgagctg 1080
accaagaacc aggtgtccct gacctgtctc gtgaaaggct tctacccctc cgacattgcc 1140
gtggaatggg agtccaacgg ccagcccgag aacaactaca agaccacccc ccctgtgctg 1200
gactccgacg gctcattctt cctgtacagc aagctgacag tggacaagtc ccggtggcag 1260
cagggcaacg tgttctcctg ctccgtgatg cacgaggccc tgcacaacca ctacacccag 1320
aagtccctga gcctgagccc tggaaaaggc ggcggaggat ctggcggagg cggttctggt 1380
ggcggctctg gcatgtccta caacctgctg ggcttcctgc agcggtcctc caacttccag 1440
agccagaaac tgctgtggca gctgaatggc accctggaat actgcctgaa ggaccggatg 1500
aacttcgaca tccccgagga aatcaagcag ctgcagcagt tccagaaaga ggacgccgcc 1560
ctgacaatct acgagatgct gcagaacatc ttcgccatct tccggcagga ctcctcctcc 1620
accggctgga acgagacaat cgtggaaaat ctgctggcca acgtgtacca ccagatcaac 1680
cacctgaaaa ccgtgctgga agagaagctg gaaaaagagg acttcacccg gggcaagctg 1740
atgtcctccc tgcacctgaa gcggtactac ggccggatcc tgcactacct gaaggccaaa 1800
gaatactccc actgcgcctg gaccatcgtg cgggtggaaa tcctgcggaa cttctacttt 1860
atcaaccggc tgaccggcta cctgaggaac tga 1893

<210> SEQ ID NO 11
<211> LENGTH: 1890
<212> TYPE: DNA
<213> ORGANISM: Artificial Sequence
<220> FEATURE:
<223> OTHER INFORMATION: Polynucleotide sequence of Atezolizumab-
      interferon beta mutein heavy chain

<400> SEQUENCE: 11
gaggtgcagc tggttgaatc tggcggagga ttggttcagc ctggcggctc tctgagactg 60
tcttgtgccg cttccggctt taccttctcc gactcctgga tccactgggt ccgacaggca 120
cctggcaaag gactggaatg ggtcgcctgg atctctcctt acggcggctc tacctactac 180
gccgactctg tgaagggcag attcaccatc tccgccgaca cctccaagaa caccgcctac 240
ctgcagatga actccctgag agccgaggac accgccgtgt actactgtgc tagaaggcat 300
tggccaggcg gcttcgatta ttggggccag ggaacactgg tcaccgtgtc ctctgcttcc 360
accaagggac cctctgtgtt ccctctggct ccttccagca agtctacctc tggcggaaca 420
gctgctctgg gctgcctggt caaggactac tttcctgagc ctgtgaccgt gtcttggaac 480
tctggcgctc tgacatccgg cgtgcacacc tttccagctg tgctgcaatc cagcggcctg 540
tactctctgt cctccgtcgt gaccgtgcct tcttctagcc tgggcaccca gacctacatc 600
tgcaatgtga accacaagcc ttccaacacc aaggtggaca agaaggtgga acccaagtcc 660
tgcgacaaga cccacacctg tcctccatgt cctgctccag aactgctcgg cggaccttcc 720
gtgttcctgt ttcctccaaa gcctaaggac accctgatga tctctcggac ccctgaagtg 780
acctgcgtgg tggtggatgt gtctcacgag gatcccgaag tgaagttcaa ttggtacgtg 840
gacggcgtgg aagtgcacaa cgccaagacc aagcctagag aggaacagta cgcctccacc 900
tacagagtgg tgtccgtgct gacagtgctg caccaggatt ggctgaacgg caaagagtac 960
aagtgcaagg tgtccaacaa ggccctgcct gctcctatcg aaaagaccat ctccaaggcc 1020
aagggccagc ctcgagaacc ccaggtttac accctgcctc caagccggga agagatgacc 1080
aagaaccagg tgtccctgac ctgcctcgtg aagggcttct acccttccga cattgccgtg 1140
gaatgggaga gcaatggcca gccagagaac aactacaaga caacccctcc tgtgctggac 1200
tccgacggct cattcttcct gtactccaag ctgaccgtgg acaagtccag atggcagcag 1260
ggcaacgtgt tctcctgctc cgtgatgcac gaggccctgc acaatcacta cacccagaag 1320
tccctgtctc tgagcccagg caaaggcgga ggtggtagcg gcggaggcgg aagtggcggt 1380
ggatctggca tgtcttacaa cctgctgggc ttcctgcagc ggtcctccaa cttccagagc 1440

-continued

```
cagaaactgc tgtggcagct gaatggcacc ctggaatact gcctgaagga ccggatgaac   1500
ttcgacatcc ccgaggaaat caagcagctg cagcagttcc agaaagagga cgccgctctg   1560
accatctacg agatgctgca gaacatcttc gccatcttcc ggcaggactc ctcctctacc   1620
ggctggaacg agacaatcgt ggaaaatctg ctggccaacg tgtaccacca gatcaaccac   1680
ctgaaaaccg tgctggaaga gaagctggaa aaagaggact tcacccgggg caagctgatg   1740
tcctctctgc acctgaagcg gtactacggc cggatcctgc actacctgaa ggccaaagaa   1800
tactcccact gcgcctggac catcgtgcgc gtggaaatcc tgcggaactt ctacttcatc   1860
aaccggctga ccggctacct gagaaactga                                    1890
```